(12) United States Patent
Kurisawa et al.

(10) Patent No.: US 10,463,646 B2
(45) Date of Patent: *Nov. 5, 2019

(54) MICELLAR POLYMER-FLAVONOID CONJUGATE NANOCOMPLEX

(71) Applicant: Agency for Science, Technology and Research, Singapore (SG)

(72) Inventors: Motoichi Kurisawa, Singapore (SG); Yongvongsoontorn Nunnarpas, Singapore (SG); Jackie Y. Ying, Singapore (SG); Joo Eun Chung, Singapore (SG); Ki Hyun Bae, Singapore (SG); Min-Han Tan, Singapore (SG); Esther Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/039,098

(22) Filed: Jul. 18, 2018

(65) Prior Publication Data

US 2019/0008830 A1    Jan. 10, 2019

Related U.S. Application Data

(62) Division of application No. 15/309,675, filed as application No. PCT/SG2015/050104 on May 8, 2015, now Pat. No. 10,052,307.

(30) Foreign Application Priority Data

May 9, 2014    (SG) ............................. 10201402244S

(51) Int. Cl.
*A61K 31/404*  (2006.01)
*C08G 65/331*  (2006.01)
(Continued)

(52) U.S. Cl.
CPC ............ *A61K 31/404* (2013.01); *A61K 9/107* (2013.01); *A61K 31/353* (2013.01);
(Continued)

(58) Field of Classification Search
CPC ...... A61K 31/404; A61K 47/59; A61K 47/60; A61K 31/704; C08G 65/3315;
(Continued)

(56) References Cited

U.S. PATENT DOCUMENTS 10,052,307 B2    8/2018   Kurisawa et al.
2017/0258926 A1  9/2017   Kurisawa et al.

FOREIGN PATENT DOCUMENTS

WO    00/74662     * 12/2000
WO    2006/124000  * 11/2006
(Continued)

OTHER PUBLICATIONS

International Search Report for PCT/SG2015/050104 (Micellar Nanocomplex, filed May 8, 2015), issued by ISA/AU, 3 pages (dated Jul. 29, 2015).

(Continued)

*Primary Examiner* — Carlos A Azpuru

(74) *Attorney, Agent, or Firm* — Choate, Hall & Stewart LLP

(57) ABSTRACT

The present invention relates to micellar nanocomplexes and a method of forming the same. The micellar nanocomplex comprises a micelle and an agent encapsulated within said micelle, where the micelle comprises a polymer-flavonoid conjugate, wherein said polymer is bonded to the B ring of said flavonoid. The micellar nanocomplex may have useful applications as a drug-delivery system.

12 Claims, 14 Drawing Sheets

(51) Int. Cl.

| | |
|---|---|
| *C08G 65/332* | (2006.01) |
| *C08G 65/333* | (2006.01) |
| *A61K 31/353* | (2006.01) |
| *A61K 47/10* | (2017.01) |
| *A61K 9/107* | (2006.01) |
| *C08L 1/02* | (2006.01) |
| *C08L 3/02* | (2006.01) |
| *C08L 5/00* | (2006.01) |
| *C08L 5/02* | (2006.01) |
| *C08L 5/16* | (2006.01) |
| *C08L 89/00* | (2006.01) |
| *A61K 47/60* | (2017.01) |
| *A61K 31/704* | (2006.01) |
| *A61K 47/59* | (2017.01) |
| *B82Y 5/00* | (2011.01) |

(52) U.S. Cl.
CPC ............ *A61K 31/704* (2013.01); *A61K 47/10* (2013.01); *A61K 47/59* (2017.08); *A61K 47/60* (2017.08); *C08G 65/331* (2013.01); *C08G 65/332* (2013.01); *C08G 65/3315* (2013.01); *C08G 65/3317* (2013.01); *C08G 65/3318* (2013.01); *C08G 65/3326* (2013.01); *C08G 65/3328* (2013.01); *C08G 65/33396* (2013.01); *C08L 1/02* (2013.01); *C08L 3/02* (2013.01); *C08L 5/00* (2013.01); *C08L 5/02* (2013.01); *C08L 5/16* (2013.01); *C08L 89/00* (2013.01); *B82Y 5/00* (2013.01); *C08L 2203/02* (2013.01)

(58) Field of Classification Search
CPC ............ C08G 65/3317; C08G 65/3318; C08G 65/3326; C08G 65/3328; C08G 65/33396
See application file for complete search history.

(56) References Cited

FOREIGN PATENT DOCUMENTS

| WO | 2013/063086 | * | 11/2006 |
|---|---|---|---|
| WO | WO-2006/124000 A1 | | 11/2006 |
| WO | WO-2009/054813 A1 | | 4/2009 |
| WO | 2015/112156 A1 | * | 9/2011 |
| WO | WO-2011/112156 A1 | | 9/2011 |
| WO | WO-2015/034436 A1 | | 3/2015 |
| WO | WO-2015/112156 A1 | | 7/2015 |

OTHER PUBLICATIONS

Written Opinion for PCT/SG2015/050104 (Micellar Nanocomplex, filed May 8, 2015), issued by ISA/AU, 6 pages (dated Jul. 29, 2015).

* cited by examiner $*P < 0.05$; $**P < 0.001$

MICELLAR POLYMER-FLAVONOID CONJUGATE NANOCOMPLEX

CROSS-REFERENCE TO RELATED APPLICATIONS

This patent application is a divisional application of U.S. patent application Ser. No. 15/309,675, filed on Nov. 8, 2016, which is the National Stage Entry of International Patent Application No. PCT/SG2015/050104, filed on May 8, 2015, which claims the benefit of priority to SG 10201402244S, filed on May 9, 2014, the entire contents of each of which are herein incorporated by reference.

TECHNICAL FIELD

The present invention generally relates to micellar nanocomplexes for drug delivery and a method of forming the same. The present invention also relates to a polymer-flavonoid conjugate comprising a polymer bonded to the B ring of a flavonoid and a method of forming the same.

BACKGROUND ART

Chemotherapy, which is one of the most common cancer treatments, uses cytotoxic drugs given via peroral and parenteral administration. The major challenge with administration of conventional anticancer drugs is their non-specific distribution in the body, leading to toxicity with serious side effects. In addition, the therapeutic effect of oral drugs is limited by their low bioavailability because the drugs must pass through digestive ducts. Over the past few decades, researchers have focused on developing drug delivery systems to overcome the limitations of the conventional drug administration by improving the pharmacokinetics and biodistribution of drugs.

In recent years, green tea catechins have been studied extensively because of their health benefits, including prevention of cardiovascular diseases and cancers. Among tea catechins, (−)-epigallalocatechin-3-gallate (EGCG) is the most abundant and has been regarded to play a major role in the beneficial effects of green tea. Numerous studies have demonstrated that EGCG possesses antioxidant, antidiabetic, antibacterial, anti-inflammatory and hypocholesterolemic effects. Moreover, it has been shown to effectively inhibit tumor growth and metastasis by targeting multiple signal transduction pathways essential for cancer cell survival.

Despite these desirable activities, clinical applications of EGCG have been limited by its poor stability and low oral bioavailability. For instance, EGCG is unstable and easily decomposed under physiological environment. It was reported that EGCG had a short half-life of less than 30 minutes in 0.05 M phosphate-buffered saline (PBS) (pH 7.4) at 37° C. In addition, most of the ingested EGCG undergo extensive hydrolysis in gastric fluid, and metabolic degradation in the gastrointestinal tract. As a result, plasma concentrations of EGCG required to achieve a desired therapeutic effect cannot be reached following oral administration.

There is therefore a need to provide a drug delivery system that overcomes or at least ameliorates, one or more of the disadvantages described above. There is also need to provide a method of forming such a drug delivery system.

SUMMARY OF INVENTION

According to a first aspect, there is provided a micellar nanocomplex comprising a micelle and an agent encapsulated within said micelle, said micelle comprising a polymer-flavonoid conjugate, wherein said polymer is bonded to the B ring of said flavonoid.

Advantageously, the micellar nanocomplexes can be used as drug delivery systems. Micellar nanocomplexes have a small size and high drug loading capacity favourable for tumor-targeted drug delivery. Further advantageously, sustained release of the agent may be achieved using micellar nanocomplexes in physiological conditions. More advantageously, the nanocomplexes may be promising delivery vehicles for a variety of water-insoluble anticancer agents. Further advantageously, the micellar nanocomplex may suppress tumor growth significantly, with reduced toxicity associated with agent administration. More advantageously, the micellar nanocomplexes may represent a unique and effective drug delivery system with synergistic therapeutic effects from the drug delivery system or the micelle carrier and the agent.

The agent may be doxorubicin. Advantageously, micellar nanocomplexes encapsulating doxorubicin may exhibit sustained drug release. This sustained drug release may be due to the strong interaction between EGCG and doxorubicin within the micellar nanocomplexes. Further advantageously, in some embodiments, only a marginal burst release was observed at the initial stage, suggesting that doxorubicin molecules were stably encapsulated in the micellar nanocomplexes. Such low drug leakage may be essential to ensure maximal therapeutic efficacy with minimal side effects, as the drug molecules encapsulated in the nanocomplexes may not leak prematurely during circulation in the blood stream. Even further advantageously, the micellar nanocomplexes may be applied for systemic administration of doxorubicin for cancer treatment.

The agent may be Sunitinib (SU) and the flavonoid may be epigallalocatechin-3-gallate (EGCG). Advantageously, the micellar nanocomplexes may exhibit a sustained release of SU. Further advantageously, in some embodiments, hardly any burst release was observed, suggesting that SU molecules were stably encapsulated in the micellar nanocomplexes.

In an embodiment, the flavonoid may be a monomeric flavonoid. In another embodiment, the flavonoid may be a dimeric flavonoid. Advantageously, micellar nanocomplex comprising the monomeric flavoid may show faster and more SU release as compared to micellar nanocomplexes comprising the dimeric flavonoid. Advantageously, there may be a stronger interaction between SU and dimeric flavonoid.

Advantageously, micellar nanocomplexes may minimise the adverse side-effects of agents such as SU by stably encapsulating the agent in their interior, and delivering them to the target site. The micellar nanocomplex may therefore provide beneficial synergistic effects between SU and EGCG.

Further advantageously, the micellar nanocomplex comprising SU may have enhanced tumor effects in vivo when compared to free SU. More advantageously, the micellar nanocomplex comprising SU may have less adverse effects in vivo when compared to free SU. Further advantageously, less dosage of the micellar nanocomplex comprising SU may be required compared to free SU to achieve the same effects. More advantageously, the inhibitory effect of the micellar nanocomplex comprising SU may be maintained for a substantial period even when the therapy is halted.

Further advantageously, the micellar nanocomplex comprising SU may lead to reduced plasma concentrations of free SU, resulting in less adverse effects of SU. Further advantageously, this reduction in plasma concentration may be due to the interaction between the flavonoid and the SU, as well as the enhanced permeability and retention (EPR) effect offered by micellar nanoparticles.

According to a second aspect, there is provided a method for forming a micellar nanocomplex comprising a micelle and an agent encapsulated within said micelle, the method comprising the steps of: (a) adding said agent in a suitable solvent to a polymer-flavonoid conjugate, wherein said polymer is bonded to the B ring of said flavonoid; and (b) allowing the self-assembly of a micelle comprising said polymer-flavonoid conjugate and encapsulation of said agent within said micelle to thereby form said micellar nanocomplex.

Advantageously, the nanocomplex is self-assembled in the presence of the polymer-flavonoid conjugate and the agent. Further advantageously, the formation of the nanocomplex was achieved by utilizing the binding property of the flavonoid with the agents.

According to a third aspect, there is provided a polymer-flavonoid conjugate comprising a polymer bonded to the B ring of a flavonoid.

Advantageously, a flavonoid is conjugated to a polymer. In an embodiment, the polymer may be polyethylene glycol (PEG). Advantageously, the polymer-based nanoparticles avoid both renal clearance and entrapment by the reticuloendothelial system (RES), allowing subsequent accumulation within tumor tissues by the EPR effect. More advantageously, PEG-stabilized micelles exhibit a prolonged plasma half-life than unmodified micelles because the PEG surface chains prevent recognition and clearance by the RES in the body. Further advantageously, PEG can be used to modify the surface of polymeric micelles and nanoparticles to produce anti-fouling surfaces.

According to a fourth aspect, there is provided a method for forming the polymer-flavonoid conjugate as defined above comprising the step of conjugating said flavonoid with said polymer via nucleophilic addition under basic conditions, wherein said polymer has a free nucleophilic group.

Advantageously, the polymer-flavonoid conjugates may be synthesized by nucleophilic addition at basic pH. Advantageously, the conjugation may be accomplished by nucleophilic addition of a nucleophilic group such as a thiol group of the polymer such as PEG at the C2' position of the B ring of the flavonoid under controlled pH conditions.

In an embodiment, the polymer is polyethylene glycol (PEG) and the free nucleophilic group is thiol. Advantageously, the electron-deficient ortho-quinone of the flavonoid such as EGCG may react with a nucleophilic group such as thiol groups. Thiol groups are present in a diverse range of biomolecules including cysteine, glutathione, and proteins. EGCG may bind covalently to cysteine residues in human erythrocyte membrane proteins and glyceraldehyde-3-phosphate dehydrogenase (GAPDH). In addition, covalent adducts of EGCG may form when oxidized in the presence of cysteine and glutathione. Further advantageously, the resulting cysteine conjugates of EGCG may exhibit higher pro-oxidant activities than EGCG, while retaining its growth inhibitory and anti-inflammatory activities. More advantageously, N-acetlycysteine-conjugated EGCG may enhance the growth inhibitory and apoptosis-inducing effects of the EGCG against murine and human lung cancer cells.

According to a fifth aspect, there is provided the use of a micellar nanocomplex comprising a micelle and an agent encapsulated within said micelle as a drug delivery vehicle, wherein said micelle comprises a polymer-flavonoid conjugate, and wherein said polymer is bonded to the B ring of said flavonoid.

According to a sixth aspect, there is provided a method of treating a tumor comprising the step of administering the micellar nanocomplex as defined above to a cancer agent.

Advantageously, the micellar nanocomplex may have a greater anticancer effect as compared to free agent. Further advantageously, micellar nanocomplexes may minimise the adverse side-effects of agents such as Suhitinib (SU) by stabling encapsulating the agent in their interior, and delivering them to the target site. Such delivery systems may also provide beneficial synergistic effects.

According to a seventh aspect, there is provided the micellar nanocomplex as defined above for treating a tumor.

According to an eighth aspect, there is provided the use of the micellar nanocomplex as defined above in the manufacture of a medicament for the treatment of a tumor.

DEFINITIONS

The following words and terms used herein shall have the meaning indicated:

The "B ring" of a flavonoid refers to an optionally substituted phenyl that is bonded to a bicyclic structure (the bicyclic structure made up of a benzene ring (A) condensed with a six membered ring (C)). The optionally substituted phenyl is bonded to the 2-position of the C ring. For the purposes of this disclosure, the rings are labelled as follows:

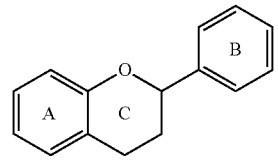

[Chem. 1]

The term "epigallocatechin gallate" refers to an ester of epigallocatechin and gallic acid, and may be used interchangeably with "epigallocatechin-3-gallate" or EGCG.

For the purposes of this application, the phrase "PEG-EGCG conjugates" refer to both PEG-mEGCG conjugates (monomeric EGCG) and PEG-dEGCG (dimeric EGCG) conjugates, unless specified.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a micellar nanocomplex will now be disclosed.

A micellar nanocomplex may comprise a micelle and an agent encapsulated within said micelle, said micelle comprising a polymer-flavonoid conjugate, wherein said polymer is bonded to the B ring of said flavonoid.

At least one flavonoid may be bonded to said polymer. At least two flavonoids may be bonded to said polymer.

The polymer may be bonded to said flavonoid via a linker. The linker may be any chemical group that may link the polymer and the flavonoid. The linker may be selected from the group consisting of a thioether, imine, amine, azo and 1,2,3-triazole group. The linker may be an alkane group. The linker may be present between any part of the polymer and any part of the flavonoid. The linker may be present between a terminus of the polymer and any part of the flavonoid.

The flavonoid may be selected from the group consisting of a monomeric flavonoid or a dimeric flavonoid. A monomeric flavonoid may comprise one flavonoid molecule. A dimeric flavonoid may comprise two flavonoid molecules linked together by a linker. One of the flavonoid molecules of the dimeric flavonoid may be linked to the polymer. Both of the flavonoid molecules of the dimeric flavonoid may be independently linked to the polymer. When one flavonoid is present in said conjugate, the flavonoid is bonded to said polymer via the B ring. When one flavonoid is bonded to said conjugate, the flavonoid is bonded to said polymer via the D ring.

When more than one flavonoid is present in said conjugate, at least one of the flavonoid is bonded to said polymer via the B ring. The other of said at least one flavonoid is bonded to said polymer via the A ring. When more than one flavonoid is present in said conjugate, at least one of the flavonoid is bonded to said polymer via the B ring. The other of said at least one flavonoid is bonded to said polymer via the B ring. When more than one flavonoid is present in said conjugate, at least one of the flavonoid is bonded to said polymer via the B ring. The other of said at least one flavonoid is bonded to said polymer via the D ring.

When more than one flavonoid is present in said conjugate, at least one of the flavonoid is bonded to said polymer via the D ring. The other of said at least one flavonoid is bonded to said polymer via the A ring. When more than one flavonoid is present in said conjugate, at least one of the flavonoid is bonded to said polymer via the D ring. The other of said at least one flavonoid is bonded to said polymer via the B ring. When more than one flavonoid is present in said conjugate, at least one of the flavonoid is bonded to said polymer via the D ring. The other of said at least one flavonoid is bonded to said polymer via the D ring.

The polymer may be a hydrophilic polymer. The hydrophilic polymer may comprise monomers selected from the group consisting of acrylamides, alkyls, oxazolines, alkenyls, imines, acrylic acids, methacrylates, diols, oxiranes, alcohols, amines, anhydrides, esters, lactones, carbonates, carboxylic acids, acrylates, hydroxyls, phosphates, terephthalate, amides and ethers.

The hydrophilic polymer may be selected from the group consisting of polyacrylamide, poly(N-isopropylacrylamide), poly(oxazoline), polyethylenimine, poly(acrylic acid), polymethacrylate, poly(ethylene glycol), poly(ethylene oxide), poly(vinyl alcohol), poly(vinylpyrrolidinone), polyethers, poly(allylamine), polyanhydrides, poly(β-amino ester), poly(butylene succinate), polycaprolactone, polycarbonate, polydioxanone, poly(glycerol), polyglycolic acid, poly(3-hydroxypropionic acid), poly(2-hydroxyethyl methacrylate), poly(N-(2-hydroxypropyl)methacrylamide), polylactic acid, poly(lactic-co-glycolic acid), poly(ortho esters), poly(2-oxazoline), poly(sebacic acid), poly(terephthalate-co-phosphate) and copolymers thereof.

The hydrophilic polymer may be a polysaccharide. The polymer may be a polysaccharide selected from the group consisting of hyaluronic acid, dextran, pullulan, chitosan, cellulose, amylose, starch, gelatin, carrageenan, cyclodextrin, dextran sulfate, Ficoll, gellan, guar gum, pectin, polysucrose, pullulan, scleroglucan, xanthan, xyloglucan and alginate.

The hydrophilic polymer may be polyethylene glycol (PEG). PEG is a synthetic polymer that has been used in biomedical applications because of its hydrophilic, flexible and biocompatible nature. Specifically, PEG has been utilized to modify the surface of polymeric micelles and nanoparticles to produce anti-fouling surfaces.

Advantageously, polyethylene glycol (PEG) was selected as the polymer to be conjugated to the flavonoid. The conjugation was accomplished by nucleophilic addition of a thiol group of PEG at the C2' position of the B ring of the flavonoid under controlled pH conditions.

The flavonoid may be selected from the group consisting of flavones, isoflavones, flavans, proanthocyanidins and anthocyanidins.

The flavones may be selected from the group consisting of apigenin, luteolin, tangeritin, chrysin, 6-hydroxyflavone, baicalein, scutellarein, wogonin, diosmin, flavoxate and 7,8-dihydroxyflavone.

The isoflavones may be selected from the group consisting of genistein, daidzein, glycitein, genistin, daidzin, glycitin, acetyl-genistin, acetyl-daidzin, acetyl-glycitin, malonyl genistin, malonyl-daidzin and malonyl-glycitin The flavans may be selected from the group consisting of (−)-epicatechin, (+)-epicatechin, (−)-catechin, (+)-catechin, epicatechin gallate, epigallocatechin, epigallocatechin gallate, Fisetinidol, Gallocatechin, Gallocatechin gallate, Mesquitol and Robinetinidol, ellagitannin, gallotannin, oolongtheanin, phlorotannin, tannin, theacitrin, theadibenzotropolone, theaflavin, theanaphthoquinone, thearubigins, theasinensin and mixtures thereof.

The anthocyanidins may be selected from the group consisting of aurantinidin, capensinidin, cyaniding, delphinidin, europinidin, hirsutinidin, malvidin, pelargondin, peonidin, petunidin, pulchellidin and rosinidin.

The agent may be a therapeutic agent. The therapeutic agent may be a chemotherapeutic agent selected from the group consisting of alkylating agents, anthracyclines, cytoskeletal disruptors, epothilones, histone deacetylase inhibitors, topoisomerase I inhibitors, topoisomerase II inhibitors, kinase inhibitors, monoclonal antibodies, antibody-drug conjugates, nucleotide analogs, precursor analogs, peptide antibiotics, platinum-based agents, retinoids, vinca alkaloids, cytokines, anti-metabolites, and vinca alkaloids derivatives, and other cytotoxics.

The chemotherapeutic agent may be selected from the group consisting of Actinomycin, Afatinib, All-trans retinoic acid, Axitinib, Azacitidine, Azathioprine, Bevacizumab, Bleomycin, Bosutinib, Bortezomib, Carboplatin, Capecitabine, Cetuximab, Cisplatin, Chlorambucil, Crizotinib, Cyclophosphamide, Cytarabine, Dasatinib, Daunorubicin, Docetaxel, Doxifluridine, Doxorubicin, Epirubicin, Epothilone A ($C_{26}H_{39}NO_6S$), Epothilone B ($C_{27}H_{41}NO_6S$), Epothilone C ($C_{26}H_{39}NO_5S$), Epothilone D ($C_{27}H_{41}NO_5S$), Epothilone E ($C_{26}H_{39}NO_7S$), Epothilone F ($C_{27}H_{41}NO_7S$), Erlotinib, Etoposide, Fluorouracil, Fostamatinib, Gefitinib, Gemcitabine, Hydroxyurea, Idarubicin, Imatinib, Irinotecan, Lapatinib, Lenvatinib, Mechlorethamine, Mercaptopurine, Methotrexate, Mitoxantrone, Nilotinib, Oxaliplatin, Paclitaxel, Panitumumab, Pazopanib, Pegaptanib, Pemetrexed, Ranibizumab, Regorafenib, Ruxolitinib, Sorafenib, Sunitinib, Trastuzumab, Teniposide, Tioguanine, Tofacitinib, Topotecan, Valrubicin, Vemurafenib, Vinblastine, Vincristine, Vindesine, Vinorelbine.

The chemotherapeutic agent may be doxorubicin.

The chemotherapeutic agent may be Sunitinib (SU). SU is a multi-targeted tyrosine kinase inhibitor and a first line therapy for clear cell renal cell carcinoma (ccRCC). Specifically, SU targets the vascular endothelial growth factor (VEGF) and platelet-derived growth factor (PDGF) receptors, which play a role in tumor angiogenesis and proliferation, leading to tumor vascularization reduction as well as cancer cell death. It has been approved for use in advanced RCC, gastrointestinal stromal tumors (GIST), and pancreatic neuroendocrine tumors (pNET). It has also been shown to have potential to cure metastatic breast cancer, advanced non-small-cell lung cancer, advanced hepatocellular carcinoma, neuroendocrine tumors, and leukemia. However, it can cause severe side effects, such as hepatic, cardiac and gastrointestinal toxicities, hypertension, skin problem, and hand-foot syndrome.

The micellar nanocomplex may have a size in the range of 30 to 300 nm, 50 to 300 nm, 100 to 300 nm, 30 to 50 nm, 30 to 100 nm, 30 to 150 nm, 150 to 300 nm, 200 to 300 nm, 250 to 300 nm, 100 to 150 nm, 100 to 200 nm, 100 to 250 nm, 130 to 180 nm, or 130 to 250 nm.

The micellar nanocomplex may have a loading efficiency of said agent present within said micelle that is more than 30%, more than 35%, more than 40%, more than 45%, more than 50%, more than 55%, more than 60%, more than 65%, more than 70%, more than 75%, or 80%.

The micellar nanocomplex may have a loading content of said agent present within said micelle in the range of 1 to 10 w/w %, 5 to 25 w/w %, 20 to 45 w/w %, 30 to 50 w/w %, 35 to 50 w/w %, 40 to 50 w/w %, 45 to 50 w/w %, 30 to 35 w/w %, 30 to 40 w/w % or 30 to 45 w/w %.

A method for forming a micellar nanocomplex may comprise a micelle and an agent encapsulated within said micelle, the method comprising the steps of:
a. adding said agent in a suitable solvent to a polymer-flavonoid conjugate, wherein said polymer is bonded to the B ring of said flavonoid; and b. allowing the self-assembly of a micelle comprising said polymer-flavonoid conjugate and encapsulation of said agent within said micelle to thereby form said micellar nanocomplex.

Step (a) may further comprise the steps of:
a. removing said solvent to form a dry film of said agent and said polymer-flavonoid conjugate; and
b. hydrating said dry film with an aqueous solvent.

The method may further comprise the step of isolating the formed micellar nanocomplex by filtration or dialysis in a suitable solvent.

A polymer-flavonoid conjugate may comprise a polymer bonded to the B ring of a flavonoid.

The polymer of the polymer-flavonoid conjugate may be selected from the group consisting of a polysaccharide, polyacrylamide, poly(N-isopropylacrylamide), poly(oxazoline), polyethylenimine, poly(acrylic acid), polymethacrylate, poly(ethylene glycol), poly(ethylene oxide), poly(vinyl alcohol), poly(vinylpyrrolidinone), polyethers, poly(allylamine), polyanhydrides, poly(β-amino ester), poly(butylene succinate), polycaprolactone, polycarbonate, polydioxanone, poly(glycerol), polyglycolic acid, poly(3-hydroxypropionic acid), poly(2-hydroxyethyl methacrylate), poly(N-(2-hydroxypropyl)methacrylamide), polylactic acid, poly(lactic-co-glycolic acid), poly(ortho esters), poly(2-oxazoline), poly(sebacic acid), poly(terephthalate-co-phosphate) and copolymers thereof.

The flavonoid of the polymer-flavonoid conjugate may be selected from the group consisting of (−)-epicatechin, (+)-epicatechin, (−)-catechin, (+)-catechin, epicatechin gallate, epigallocatechin, epigallocatechin gallate, Fisetinidol, Gallocatechin, Gallocatechin gallate, Mesquitol and Robinetinidol, ellagitannin, gallotannin, oolongtheanin, phlorotannin, tannin, theacitrin, theadibenzotropolone, theaflavin, theanaphthoquinone, thearubigins, theasinensin and mixtures thereof.

The polymer may be conjugated to a flavonoid in the polymer-flavonoid conjugate via a linker selected from the group consisting of a thioether, imine, amine, azo and 1,2,3-triazole group. The linker may be an alkane group. The linker may be present between any part of the polymer and any part of the flavonoid. The linker may be present between a terminus of the polymer and any part of the flavonoid.

The polymer of the polymer-flavonoid conjugate may be poly(ethylene glycol), said flavonoid of the polymer-flavonoid conjugate may be epigallocatechin-3-gallate and said linker of the polymer-flavonoid conjugate may be thioether.

The polymer-flavonoid may have the following formula

[Chem. 2]

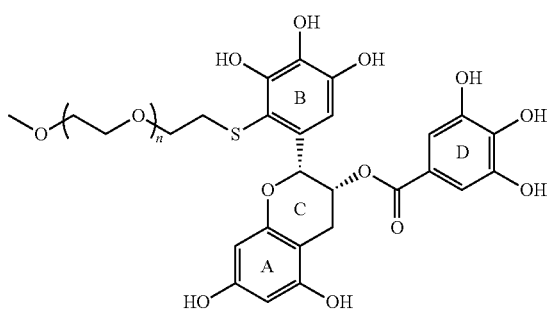

wherein n is in the range of 20 to 910.

A method for forming the polymer-flavonoid conjugate may comprise the step of conjugating said flavonoid with said polymer via nucleophilic addition under basic conditions, wherein said polymer has a free nucleophilic group.

The nucleophilic group may be selected from the group consisting of a sulfhydryl, amine, carbonyl, carboxylic acid, azide, halogen, alkyne and alkene. The nucleophilic group may be selected from the group consisting of a thiol, an amine, a diazoalkane and an azide.

The nucleophilic group may be a thiol. EGCG may undergo oxidation in the presence of oxygen to form an ortho-quinone via a pathway involving semiquinone radicals and reactive oxygen species. The electron-deficient ortho-quinone of EGCG may react with a nucleophilic thiol group present in diverse biomolecules including cysteine, glutathione, and proteins. EGCG may bind covalently to cysteine residues in human erythrocyte membrane proteins and glyceraldehyde-3-phosphate dehydrogenase (GAPDH). Covalent adducts of EGCG may be formed when oxidized in the presence of cysteine and glutathione. The resulting cysteine conjugates of EGCG may exhibit higher pro-oxidant activities than EGCG, while retaining its growth inhibitory and anti-inflammatory activities. Furthermore, N-acetylcysteine-conjugated EGCG may enhance the growth inhibitory and apoptosis-inducing effects of EGCG against murine and human lung cancer cells.

The conjugating step may be undertaken at a reaction time of between about 1 hour to 24 hours, about 1 hour to 2 hours, about 1 hour to 4 hours, about 1 hour to 8 hours, about 1 hour to 12 hours, about 2 hours to 4 hours, about 2 hours to 8 hours, about 2 hours to 12 hours, about 2 hours to 24 hours, about 4 hours to 8 hours, about 4 hours to 12 hours, about 4 hours to 24 hours, about 8 hours to 12 hours, about 8 hours to 24 hours or about 12 hours to 24 hours.

The method may further comprise the step of conducting the conjugating step in a solvent that substantially prevents aggregation of said flavonoid.

The method may further comprise the step of adding a scavenging agent to prevent $H_2O_2$-mediated oxidation of said nucleophilic group to thereby increase the efficiency of said conjugating step.

The basic conditions may be in the pH range of more than 7 to 10, more than 8 to 10, more than 9 to 10, more than 7 to 11, more than 8 to 11, more than 9 to 11, more than 10 to 11, more than 7, more than 8, more than 9, more than 10 or more than 11.

Use of a micellar nanocomplex may comprise a micelle and an agent encapsulated within said micelle as a drug delivery vehicle, wherein said micelle comprises a polymer-flavonoid conjugate, and wherein said polymer is bonded to the B ring of said flavonoid.

The micellar nanocomplex may deliver the encapsulated agent to a targeted tumor site in vivo.

A method of treating cancer may comprise the step of administering the micellar nanocomplex to a cancer patient. A method of treating a tumor may comprise the step of administering the micellar nanocomplex to a cancer patient.

The micellar nanocomplex may be administered parenterally, by inhalation spray, topically, rectally, nasally, buccally, vaginally, via an implanted reservoir, by injection, subdermally, intraperitoneally, transmucosally, orally or in an ophthalmic preparation.

The parenteral administration may comprise subcutaneously, intracutaneously, intravenously, intramuscularly, intraarticularly, intraarterially, intrasynovially, intrasternally, intrathecally, intralesionally and by intracranial injection or infusion techniques.

The agent present in said micellar nanocomplex may be administered at a dose of about 1 to about 80 mg/kg per day, about 1 to about 2 mg/kg per day, about 1 to about 5 mg/kg per day, about 1 to about 10 mg/kg per day, about 1 to about 20 mg/kg per day, about 1 to about 50 mg/kg per day, about 2 to about 5 mg/kg per day, about 2 to about 10 mg/kg per day, about 2 to about 20 mg/kg per day, about 2 to about 50 mg/kg per day, about 2 to about 80 mg/kg per day, about 5 to about 10 mg/kg per day, about 5 to about 20 mg/kg per day, about 5 to about 50 mg/kg per day, about 5 to about 80 mg/kg per day, about 10 to about 20 mg/kg per day, about 10 to about 50 mg/kg per day, about 10 to about 80 mg/kg per day, about 20 to about 50 mg/kg per day, about 20 to about 80 mg/kg per day or about 50 to about 80 mg/kg per day.

The cancer patient may be suffering from a cancer selected from the group consisting of adrenocortical carcinoma, AIDS-related lymphoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, bronchial cancer, bronchioalveolar carcinoma, Burkitt lymphoma, cervical cancer, colon cancer, colorectal cancer, craniopharyngioma, cutaneous T-cell lymphoma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, head and neck cancer, heart cancer, hepatocellular cancer, Hilar cholangiocarcinoma, Hodgkin's lymphoma, hypopharyngeal cancer, intraocular melanoma, islet cell tumor, Kaposi sarcoma, Langerhans cell histiocytosis, laryngeal cancer, lip cancer, lymphoma, macroglobulinemia, malignant fibrous histiocytoma, medulloblastoma, medulloepithelioma, melanoma, Merkel cell carcinoma, mesothelioma, endocrine neoplasia, multiple myeloma, mycosis fungoides, myelodysplasia, myelodysplastic/myeloproliferative neoplasms, myeloproliferative disorders, nasal cavity cancer, nasopharyngeal cancer, neuroblastoma, non-Hodgkin's lymphoma, oral cancer, oropharyngeal cancer, osteosarcoma, ovarian clear cell carcinoma, ovarian epithelial cancer, ovarian germ cell tumor, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, primary central nervous system lymphoma, prostate cancer, rectal cancer, renal cell cancer, respiratory tract cancer with chromosome 15 changes, retinoblastoma, rhabdomyosarcoma, salivary gland cancer, Sezary syndrome, small intestine cancer, soft tissue sarcoma, squamous cell carcinoma, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenstrom macroglobulinemia, and Wilms tumor.

The tumor patient may be suffering from a cancer selected from the group consisting of adrenocortical carcinoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, bronchial cancer, bronchioalveolar carcinoma, cervical cancer, colon cancer, colorectal cancer, craniopharyngioma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, head and neck cancer, heart cancer, hepatocellular cancer, Hilar cholangiocarcinoma, hypopharyngeal cancer, intraocular melanoma, islet cell tumor, Kaposi sarcoma, Langerhans cell histiocytosis, laryngeal cancer, lip cancer, acroglobulinemia, malignant fibrous histiocytoma, medulloblastoma, medulloepithelioma, melanoma, Merkel cell carcinoma, mesothelioma, endocrine neoplasia, multiple myeloma, mycosis fungoides, myelodysplasia, myelodysplastic/myeloproliferative neoplasms, myeloproliferative disorders, nasal cavity cancer, nasopharyngeal cancer, neuroblastoma, oral cancer, oropharyngeal cancer, osteosarcoma, ovarian clear cell carcinoma, ovarian epithelial cancer, ovarian germ cell tumor, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, prostate cancer, rectal cancer, renal cell cancer, respiratory tract cancer with chromosome 15 changes, retinoblastoma, rhabdomyosarcoma, salivary gland cancer, Sezary syndrome, small intestine cancer, soft tissue sarcoma, squamous cell carcinoma, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenstrom macroglobulinemia, and Wilms tumor.

The micellar nanocomplex may be for treating cancer. The micellar nanocomplex may be for treating a tumor.

Use of the micellar nanocomplex may be in the manufacture of a medicament for the treatment of cancer. Use of the micellar nanocomplex may be in the manufacture of a medicament for the treatment of a tumor.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Figure 1:
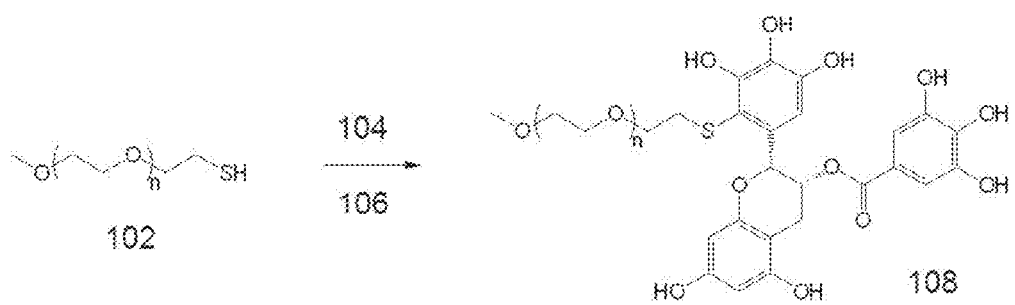
FIG. 1 is a synthetic scheme of PEG-mEGCG conjugate (108). Thiol-functionalized PEG (PEG-SH) (102) was conjugated to EGCG (104) in a 1:3 (v/v) mixture of DMSO and water at basic pH (106).

Non-limiting examples of the invention and a comparative example will be further described in greater detail by reference to specific Examples, which should not be construed as in any way limiting the scope of the invention.

Example 1: Materials And Cell Culture

Materials

Methoxy-polyethylene glycol with a thiol end terminal (PEG-SH, M$_w$=5000 Da) was obtained from JenKem Technology (China). Methoxy-polyethylene glycol with an aldehyde end terminal (PEG-CHO, Mw=5000 Da) was obtained from NOF Co., Japan. (−)-Epigallocatechin-3-gallate (EGCG, >95% purity) was obtained from Kurita Water Industries (Tokyo, Japan). Sodium pyruvate solution (100 mM) was purchased from Invitrogen (Singapore). PBS saline without Ca$^{2+}$ and Mg$^{2+}$ (150 mM, pH 7.3) was supplied by the media preparation facility at Biopolis, Singapore. DMSO and triethylamine (TEA) were purchased from Sigma-Aldrich (Singapore). Doxorubicin hydrochloride (DOX-HCl) was purchased from Boryung Pharm. Inc. (Korea). SU (free base form) were purchased from BioVision (US). All other chemicals were of analytical grade.

Cell Culture

Human renal cell carcinoma cells A498 were obtain from American Type Culture Collection (ATCC, Manassas, Va., USA), and cultured in Dulbecco's Modified Eagle's Medium supplemented with 10% fetal bovine serum, 1% penicillin-streptomycin, 2 mM of glutamine and 0.1 mM of non-essential amino acids. The stable A498 cell clone expressing luciferase gene (A498-luc) was generated as described. Briefly, A498 cells were seeded in a six-well plate at a density of $5\times10^5$ cells/well and transfected with pRC-CMV2-luc plasmid using Lipofectamine 2000 (Invitrogen, Carlsbad, Calif., USA). After 1 day, transfected cells were transferred to a 100-mm cell culture dish, and 1 mg ml$^{-1}$ geneticin was added to the medium to select the resistant cells. After 1 week of selection, resistant cells were seeded in a 96-well plate at a density of 1 cell/well to form colonies. A total of 10 colonies were selected and expanded, and the luciferase activity was measured with a Promega Kit (Madison, Wis., USA) in a single-tube luminometer (Berthold Lumat LB 9507, Bad Wildbad, Germany). A clone with the highest luciferase activity was chosen and maintained with 500 mg ml$^{-1}$ geneticin.

Example 2: The PEG-EGCG Conjugates

In this study, two types of PEG-EGCG conjugates were used to form micellar nanocomplexes, PEG-mEGCG and PEG-dEGCG, which have one and two EGCG moieties at one end of the PEG, respectively.

Synthesis of PEG-mEGCG Conjugate

PEG-mEGCG conjugate was synthesized by conjugating EGCG to PEG containing a thiol end terminal. Typically, EGCG (18.3 mg, 40 µmol) was dissolved in 20 mL of a 1:1 (v/v) mixture of PBS and DMSO. PEG-SH ($M_w$=5000 Da, JenKem Technology, China) (100 mg, 20 µmol) was separately dissolved in 20 mL of PBS. The PEG-SH solution was added dropwise to a stirred solution of EGCG. As a control experiment, unmodified PEG solution was added to a stirred solution of EGCG at the same concentration. The resulting mixture has pH of 8.4. The mixture was stirred for 7 hours at 25° C. To this solution, 1.6 mL of 10% acetic acid was added to adjust the pH to 4 to stop the reaction. The resulting solution was transferred to dialysis tubes with a molecular weight cutoff (MWCO) of 1,000 Da. The tubes were dialyzed against deionized water. The purified solution was lyophilized to obtain PEG-mEGCG conjugate. The structure of PEG-mEGCG conjugate was confirmed by $^1$H NMR spectroscopy. The dried PEG-mEGCG conjugate was dissolved in $D_2O$ at a concentration of 20 mg mL$^{-1}$ and then analyzed with a Bruker AV-400 NMR spectrometer operating at 400 MHz. Yield: 89%. $^1$H NMR ($D_2O$): δ 2.9 (t, H-α from PEG), 3.4 (s, H-γ from PEG), 3.5-3.8 (m, protons of PEG), 5.5 (s, H-2 of C ring), 5.85 (s, H-3 of C ring), 6.15 (d, H-6 and H-8 of A ring), 6.9 (s, H-6' of B ring), 7.05 (s, H-2" and H-6" of D ring).

FIG. 1 illustrates the synthetic scheme of PEG-mEGCG conjugates (108). Thiol-functionalized PEG (PEG-SH) (102) was incubated with a 2-fold molar excess of EGCG (PEG-SH:EGCG=1:2) (104) in a 1:3 (v/v) DMSO and water mixture at basic pH (106). It has been reported that pH critically influences the autooxidation process of EGCG. In the basic pH range of 7-9.5, the gallyl moiety on the B ring is more susceptible to autoxidation than the gallate moiety on the D ring. As a result, only the gallyl moiety on the B ring forms an ortho-quinone. Under strong alkaline conditions (pH>10), the gallate moiety on the D ring can also be autoxidized to form an ortho-quinone. In the present study, the reaction was conducted at pH 8.4 to allow for formation of an ortho-quinone only at the B ring of EGCG. Subsequent nucleophilic addition of PEG-SH to the ortho-quinone produced PEG-mEGCG conjugates linked through a covalent thioether bond.

It is noteworthy that the conjugation reaction proceeded in the presence of dimethyl sulfoxide (DMSO). Since EGCG would undergo aggregation upon contact with PEG in aqueous solution, it should avoid aggregation during the conjugation of EGCG to PEG-SH. It was found that DMSO effectively prevented aggregation. Based on this finding, the conjugation reaction was performed in a mixture of DMSO and water. In addition, sodium pyruvate was used as a scavenger for $H_2O_2$ generated during the autoxidation of EGCG. Since sodium pyruvate protects free thiol groups against $H_2O_2$-mediated oxidation, it can increase the number of PEG-SH molecules available for a conjugation reaction with EGCG. The PEG-mEGCG conjugate obtained was purified by dialysis under a nitrogen atmosphere and then lyophilized to obtain a white powder.

UV-Vis Characterization of PEG-mEGCG Conjugate

Figure 2:
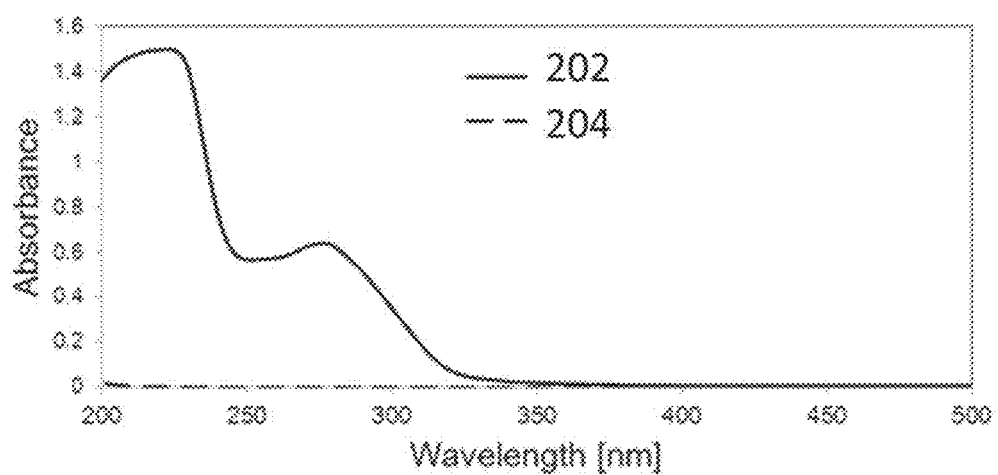
FIG. 2 is a UV-Vis spectra of PEG-EGCG conjugate (202) and PEG (204) dissolved in deionized water at a concentration of 0.5 mg mL$^{-1}$.

The PEG-mEGCG conjugates were characterized using ultraviolet-visible (UV-Vis) spectroscopy (FIG. 2).

UV-Vis spectra of PEG-mEGCG conjugates were measured on a Hitachi U-2810 spectrophotometer (Japan). For UV-Vis spectroscopy, the dried PEG-mEGCG conjugate and PEG were dissolved in deionized water at a concentration of 0.5 mg mL$^{-1}$. Unlike the unmodified PEG (204), PEG-mEGCG conjugates (202) were shown to have an intense UV absorption peak at 280 nm, indicative of a successful conjugation of EGCG. Moreover, the UV absorption band at 425 nm corresponding to EGCG dimers and other oxidative products was not observed.

HPLC Characterization of PEG-mEGCG Conjugate

Figure 3:
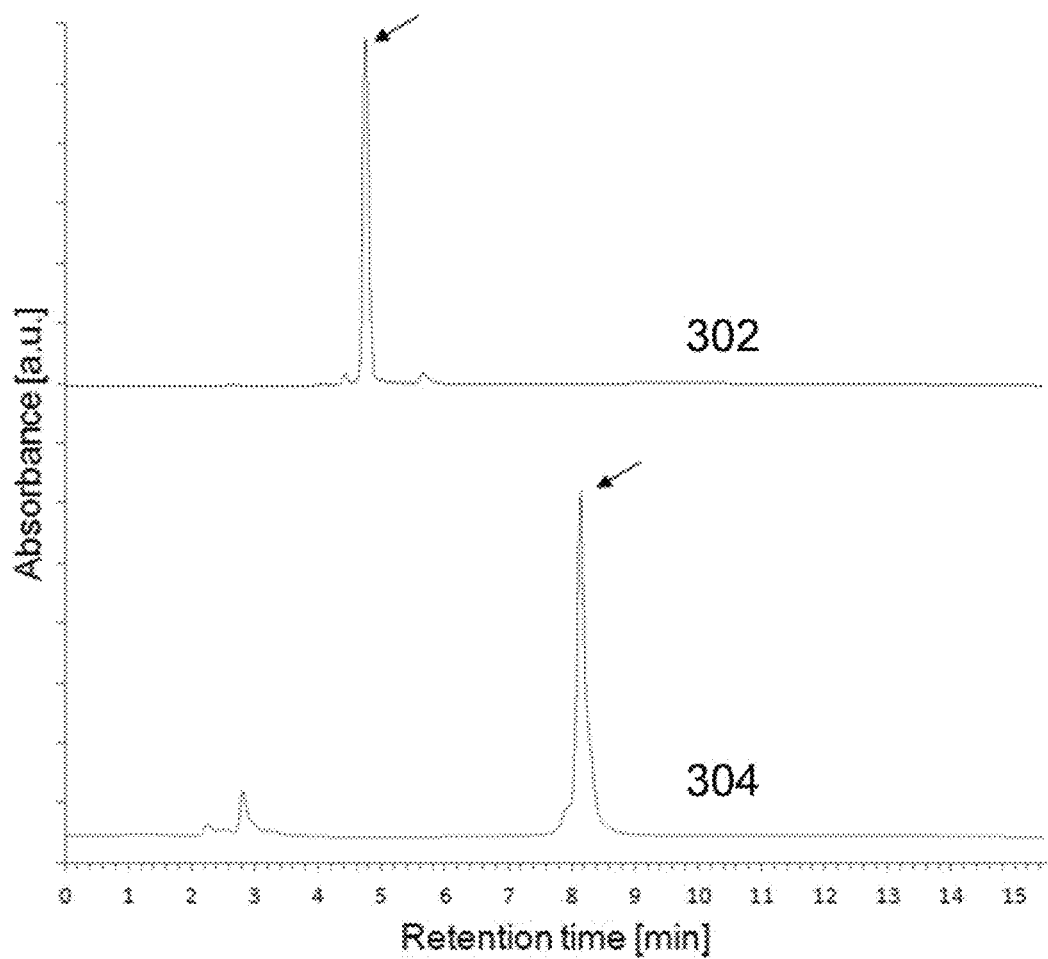
FIG. 3 refers to HPLC chromatograms of EGCG (302) and PEG-mEGCG conjugate (304). The arrows indicate the peaks of samples monitored at 280 nm.
Figure 4:
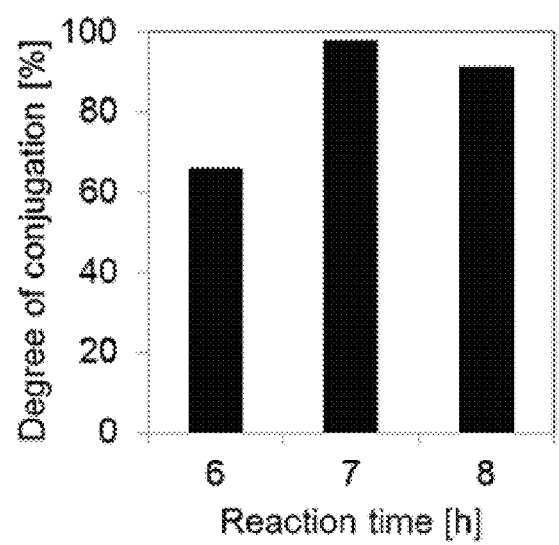
FIG. 4 is the degree of conjugation of PEG-mEGCG conjugates as a function of reaction time.

PEG-mEGCG conjugate was also assessed by reversed-phase high-performance liquid chromatography (HPLC). Reversed-phase HPLC was performed using a Waters 2695 separations module equipped with a Spirit™ C18 organic column (5 µm, 4.6×250 mm i.d., AAPPTec). EGCG, PEG/EGCG mixture, and PEG-mEGCG conjugates were dissolved in deionized water at a concentration of 1 mg mL$^{-1}$. The samples were eluted with a solvent mixture of 1% acetic acid in acetonitrile and 1% acetic acid in water at a flow rate of 1 mL/minutes at 25° C. For the mobile phase, the acetonitrile:water volume ratio gradually increased from 3:7 at 0 minutes to 4:6 at 10 minutes. The eluted samples were monitored at 280 nm. The degree of EGCG conjugation was determined by comparing the integrated peak area with those obtained from a series of EGCG standard solutions of various concentrations. As shown in FIG. 3, EGCG (302) was eluted at a retention time of 4.8 min, while PEG-mEGCG conjugate (304) was eluted at 8 min. This dramatic shift in the retention time could be explained by the attachment of a hydrophilic PEG chain to EGCG. In addition, no EGCG peak was observed in the HPLC chromatogram of the PEG-mEGCG conjugates, suggesting that unreacted EGCG molecules were completely removed by dialysis. The degree of EGCG conjugation increased from ~63 to 98% as the reaction time increased from 6 to 7 hours (FIG. 4). However, when the reaction time was 8 h, the degree of conjugation was slightly decreased, presumably because EGCG dimers and other oxidative products began to form. Hence, the optimum reaction time was 7 h.

$^1$H NMR Characterization of PEG-mEGCG Conjugate

Figure 5:
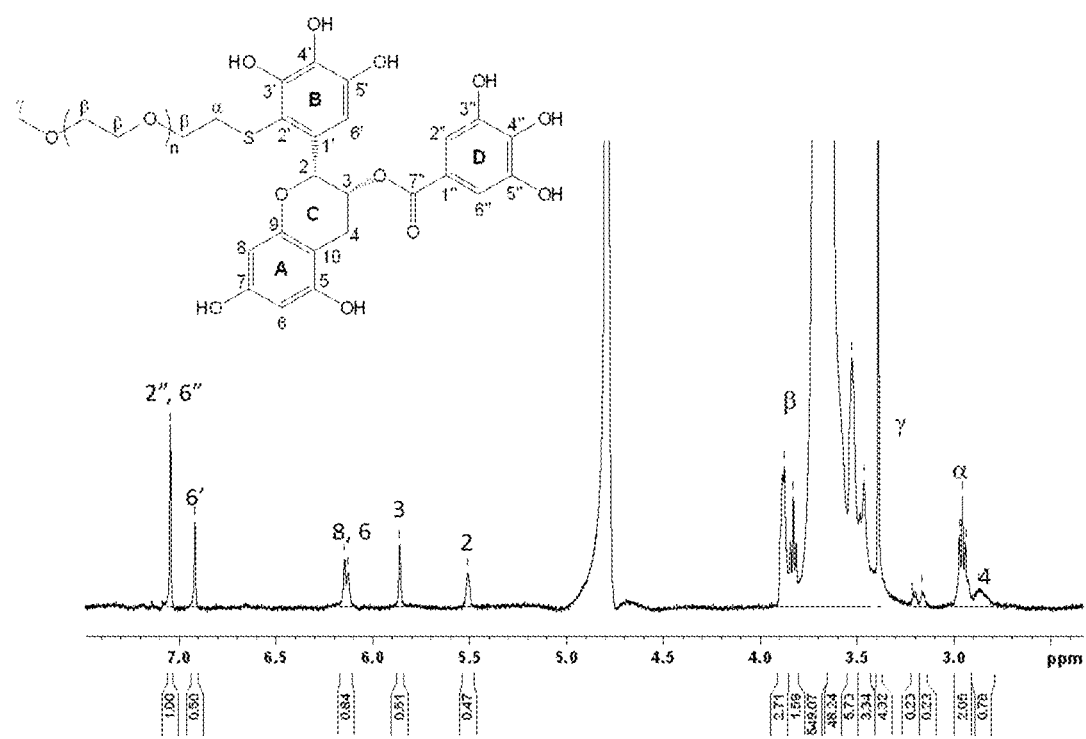
FIG. 5 is a $^1$H NMR spectrum of PEG-mEGCG conjugate dissolved in D$_2$O.

The structure of PEG-mEGCG conjugates was determined by $^1$H nuclear magnetic resonance (NMR) spectroscopy. As shown in FIG. 5, PEG-mEGCG conjugates displayed proton signals for the A ring (H-6 and H-8 at δ=6.15), C ring (H-2 at δ=5.5 and H-3 at δ=5.85), and D ring (H-2" and H-6" at δ=7.1). The proton signals arising from the A, C and D rings were similar to those of unmodified EGCG, suggesting that these moieties remained unchanged during the conjugation reaction. In contrast, the proton signals for the B ring were shifted from 6.5 to 6.9 ppm after the conjugation reaction. This significant shift in the proton signals was likely attributed to the attachment of PEG-SH to the C2' position of B ring. In addition, the NMR peak for the B ring was shown to have half of the area under the peak for the D ring, indicating that one proton on the B ring disappeared after the conjugation reaction. The observed phenomenon was in agreement with the previous report, whereby the formation of 2'-cysteinyl EGCG caused the disappearance of H-2' atom from the B ring. The above results revealed that only one PEG molecule could be conjugated specifically to the C2' position of the B ring of EGCG.

Synthesis of PEG-dEGCG Conjugate

PEG-dEGCG conjugates were synthesized by conjugating EGCG to PEG with an aldehyde end group (PEG-CHO). The PEG-CHO ($M_w$=5000 Da, NOF Co., Japan) (1.75 g) and EGCG (3.25 g, 7.09 mmol) were separately dissolved in a mixture of acetic acid, water and DMSO. The reaction was initiated with the dropwise addition of the PEG-CHO solution, and was conducted at 20° C. for 72 h. The resultant solution was dialyzed (MWCO=3500 Da) against deionized water. The purified solution was lyophilized to obtain PEG-dEGCG conjugates.

Example 3: The Doxorubicin/PEG-mEGCG Conjugate

For cancer therapy applications, PEG-mEGCG conjugates were designed to form micellar nanocomplexes capable of carrying a large number of anticancer drugs in the interior. In this study, PEG-mEGCG micellar nanocomplexes were utilized as a delivery vehicle for doxorubicin. Doxorubicin is one of the most widely used chemotherapeutic agents and exhibits strong cytotoxic activity against various types of cancers, such as leukemia, breast, ovarian and lung cancers. However, it can cause severe cardiotoxicity and increase the risk of congestive heart failure, heart arrhythmias, hypotension and other side effects. It is envisioned that PEG-mEGCG micellar nanocomplexes can minimize such adverse side effects by stably encapsulating drug molecules in their interior and releasing them in a sustained manner.

Formation of Doxorubicin/PEG-mEGCG Micellar Nanocomplexes

Doxorubicin/PEG-mEGCG micellar nanocomplexes were prepared using a dialysis method. Briefly, 5 mg of DOX-HCl was dissolved in 4.5 mL of dimethylformamide. To this solution, TEA was added at a TEA:DOX-HCl molar ratio of 5:1. This mixture was vortexed for 30 minutes to form deprotonated doxorubicin (DOX). The resulting DOX solution was mixed with PEG-mEGCG conjugates dissolved in 0.5 mL of dimethylformamide at varying PEG-mEGCG/DOX weight ratios. This mixture was vortexed for 90 minutes and then transferred to dialysis tubes with a MWCO of 2,000 Da. The tubes were dialyzed against deionized water for 24 hours to obtain the doxorubicin/PEG-mEGCG micellar nanocomplexes.

Characterization of Doxorubicin/PEG-mEGCG Micellar Nanocomplexes

The hydrodynamic diameters, polydispersity indexes, and zeta potentials of doxorubicin/PEG-mEGCG micellar nanocomplexes were evaluated by dynamic light scattering (Zetasizer Nano ZS, Malvern, UK). The measurement was performed in triplicate in water at 25° C. To measure the loading amount of doxorubicin, 20 μL of the nanocomplexes dispersed in water was mixed with 980 μL of dimethylformamide to extract the doxorubicin. The absorbance of doxorubicin at 480 nm was measured using a Hitachi U-2810 spectrophotometer (Japan). The drug loading efficiency and loading content were determined by comparing the absorbance values with those obtained from a series of doxorubicin standard solutions with varying concentrations.

Figure 6:
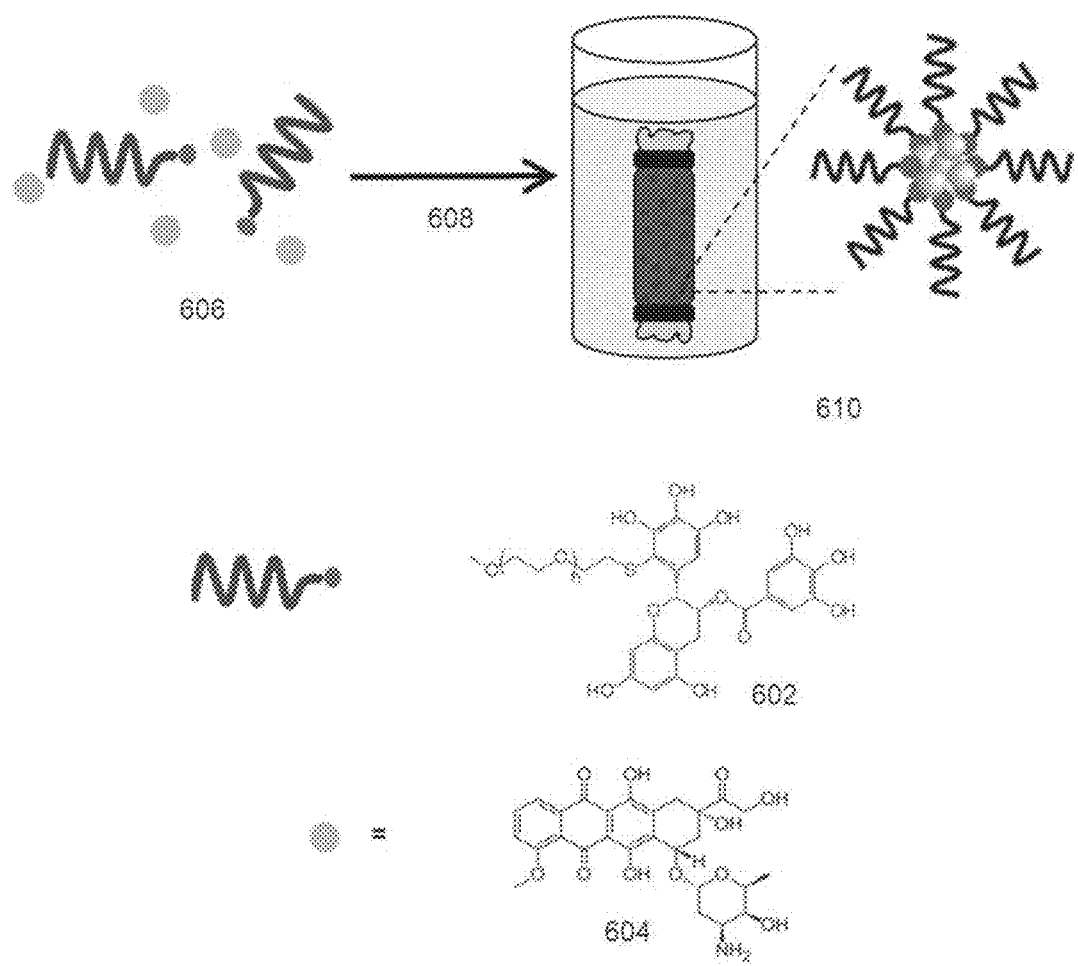
FIG. 6 is a schematic showing the formation of doxorubicin/PEG-mEGCG micellar nanocomplexes.

FIG. 6 illustrates the formation of doxorubicin/PEG-mEGCG micellar nanocomplexes. PEG-mEGCG conjugates (602) and doxorubicin (604) were co-dissolved in dimethylformamide (606). This mixture was dialyzed against distilled water (608). As the organic solvent was removed from the dialysis tubes, the hydrophobic EGCG moieties in the conjugates started to self-assemble to form a micellar core surrounded by a shell of the hydrophilic PEG chains (610). Simultaneously, doxorubicin molecules were also partitioned into the hydrophobic micellar core. It was also reported that doxorubicin molecules were easily stacked together in aqueous solution because of π-π interaction between the planar anthracycline rings. Since EGCG has a polyphenol structure capable of interacting with doxorubicin via π-π stacking, it was anticipated that EGCG enriched in the core of micellar nanocomplexes might provide a favorable environment for the entrapment of doxorubicin within them. Furthermore, the surface-exposed PEG chains could form a protective shell around the micellar nanocomplexes to avoid clearance by the reticuloendothelial system, thereby allowing for prolonged circulation in the blood stream.

Figure 7:
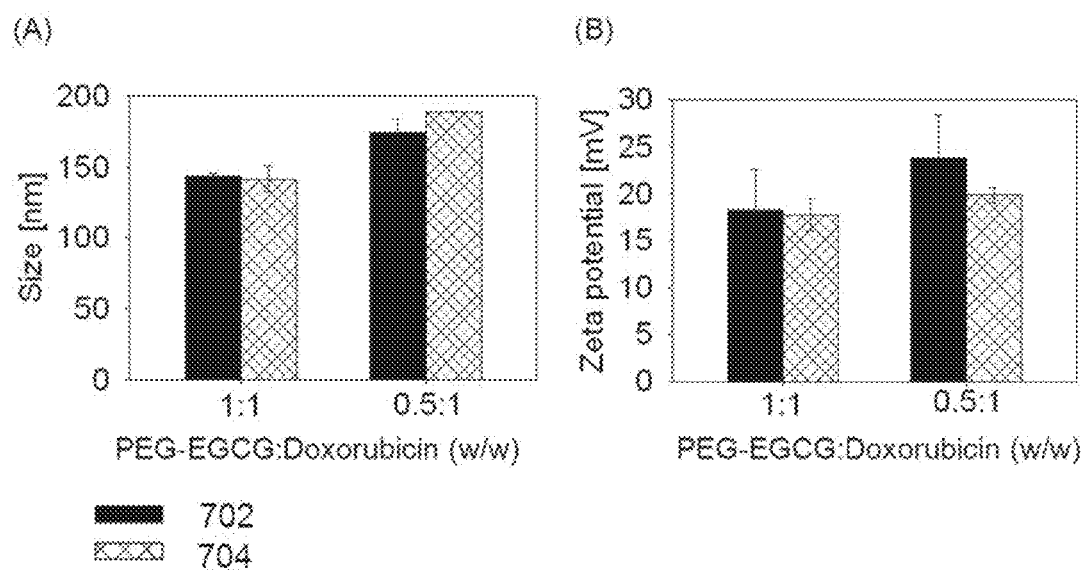
FIG. 7 refers to graphs showing (A) Size and (B) zeta potential of doxorubicin/PEG-mEGCG micellar nanocomplexes prepared at different PEG-mEGCG:doxorubicin weight ratios. The size and zeta potential of as-prepared nanocomplexes (black bars, 702) were compared to those of reconstituted nanocomplexes (crossed bars, 704).

The size and surface charge of doxorubicin/PEG-mEGCG micellar nanocomplexes were characterized by dynamic light scattering (DLS) analysis. FIG. 7 refers to graphs showing (A) size and (B) zeta potential of doxorubicin/PEG-mEGCG micellar nanocomplexes.

FIG. 7A shows the hydrodynamic diameter of the micellar nanocomplexes prepared at different weight ratios of PEG-mEGCG to doxorubicin. Notably, the nanocomplexes were produced with a size range of 130-180 nm. Such a small size is favorable in achieving prolonged circulation in the blood stream and tumor targeting via the enhanced permeability and retention (EPR) effect. The micellar nanocomplexes formed at a PEG-mEGCG:doxorubicin weight ratio of 0.5:1 have a larger diameter than those formed at 1:1. The entrapment of higher amounts of doxorubicin was likely responsible for the formation of larger micellar nanocomplexes. The nanocomplexes were highly monodisperse, as evident from small polydispersity index (PDI) value falling within the range of 0.1-0.2.

As shown in FIG. 7B, the micellar nanocomplexes had a positive zeta potential in the range of +15-25 mV. This cationic surface charge was attributed to the encapsulation of positively charged doxorubicin molecules within the nanocomplexes. We also evaluated whether the micellar nanocomplexes maintained their structural integrity during a freeze-drying process. Freeze-drying is one of the most popular techniques used for the long-term storage of colloidal nanoparticles. The nanocomplexes were lyophilized and then re-dispersed in deionized water at the same concentration. The reconstituted nanocomplexes were found to retain the original particle size and surface charge even without any lyoprotectants. Such high colloidal stability would be advantageous in the clinical translation and commercialization of the micellar nanocomplexes.

Figure 8:
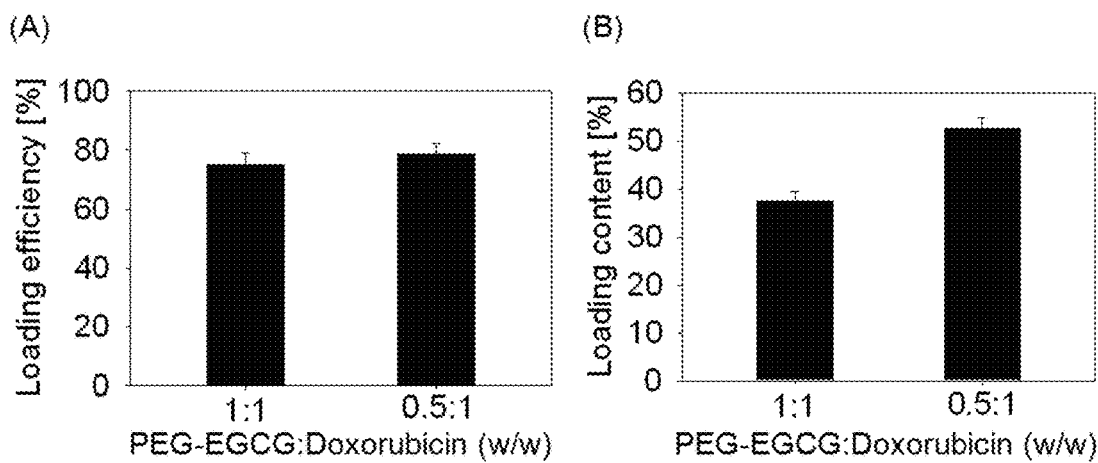
FIG. 8 refers to graphs showing (A) Drug loading efficiency and (B) loading content of doxorubicin/PEG-mEGCG micellar nanocomplexes prepared with different PEG-mEGCG:doxorubicin weight ratios.

FIG. 8 shows the drug loading efficiency and loading content of doxorubicin/PEG-mEGCG micellar nanocomplexes. The drug loading efficiency was higher than 75%, indicating that doxorubicin was efficiently incorporated in the PEG-mEGCG nanocomplexes. As the PEG-mEGCG:doxorubicin weight ratio decreased, both drug loading efficiency and loading content increased. The observed loading content (35-50 w/w %) was significantly higher than those achieved with other polymeric micellar systems. The π-π stacking and/or hydrophobic interactions between EGCG and doxorubicin might have played an important role in the high drug loading capacity of the PEG-mEGCG micellar nanocomplexes.

Doxorubicin Release Study

For release experiments, 0.5 mL of doxorubicin-loaded nanocomplexes (2 mg mL$^{-1}$) was placed in dialysis tubes with a MWCO of 2,000 Da. The tubes were immersed in 25 mL of PBS in a shaking incubator at 37° C. At a given time point, 1 mL of the release medium was collected and then replaced with an equivalent volume of fresh PBS. The amount of doxorubicin released into the medium was determined by measuring the absorbance of doxorubicin at 480 nm using a Hitachi U-2810 spectrophotometer (Japan).

Figure 9:
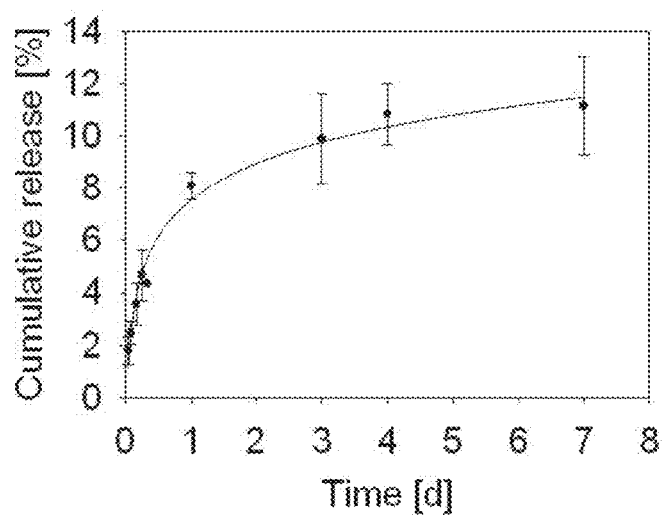
FIG. 9 shows in vitro drug release profile of doxorubicin/PEG-mEGCG micellar nanocomplexes in PBS (pH 7.3) at 37° C. PEG-mEGCG:doxorubicin weight ratio=1:1.

The drug release profile of doxorubicin/PEG-mEGCG micellar nanocomplexes was also investigated at physiological temperature and pH. As shown in FIG. 9, the micellar nanocomplexes exhibited a sustained release of doxorubicin in PBS. Approximately 11% of the loaded doxorubicin was released within 7 days. The observed release rate is considerably lower than that of the other doxorubicin delivery systems reported previously. This sustained drug release was probably caused by the strong interaction between EGCG and doxorubicin within the micellar nanocomplexes. In addition, only a marginal burst release was observed at the initial stage, suggesting that doxorubicin molecules were stably encapsulated in the micellar nanocomplexes. Such low drug leakage would be essential to ensure maximal therapeutic efficacy with minimal side effects, as the drug molecules encapsulated in the nanocomplexes would not leak prematurely during circulation in the blood stream. Taken together, these results demonstrated that PEG-mEGCG micellar nanocomplexes could be applied for systemic administration of doxorubicin for cancer treatment.

Example 4: The SU/PEG-EGCG Conjugates

Formation of SU/PEG-EGCG Micellar Nanocomplexes

Figure 10:
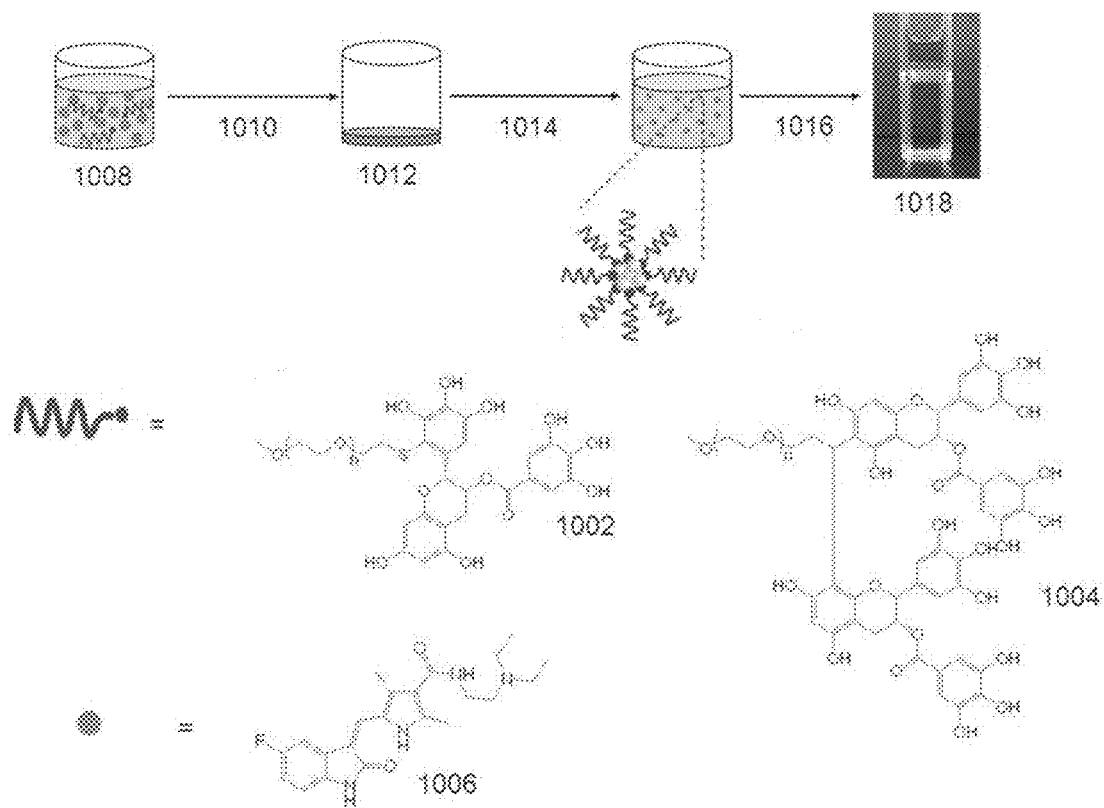
FIG. 10 shows a schematic illustration of the formation of SU/PEG-EGCG micellar nanocomplexes.

FIG. 10 illustrates the formation of SU/PEG-EGCG conjugates using the solid dispersion method. Briefly, 2 mg of SU (1006) was dissolved in 1 mL of chloroform. Then SU solution was added to PEG-EGCG conjugates (either PEG-mEGCG (1002) or PEG-dEGCG (1004) in glass vials at varying PEG-EGCG:SU weight ratios (1008) and vortexed. Then chloroform of the solution was evaporated under reduced pressure (1010). The resulting thin film of PEG-EGCG and SU mixture (1012) was hydrated by adding 2 mL of water to the surface (1014), and incubated at ambient temperature for 24 h. As the resulting solid film was hydrated, the PEG-EGCG self-assembled to form micellar nanocomplexes by isolation of SU and EGCG moieties from the hydrated PEG chains. The SU/PEG-EGCG micellar nanocomplexes solution was then filtered (1016) through 0.8-μm filter (Sartorius Stedim Biotech GmbH, Germany) to remove any residual free drugs yielding the transparent SU/PEG-EGCG micellar nanocomplex solution (1018). For in vivo studies, the SU/PEG-EGCG micellar nanocomplexes solution was further filtered using a 0.2-μm filter (Sartorius Stedim Biotech GmbH, Germany).

It should be noted that PEG-EGCG conjugates refer to both PEG-mEGCG and PEG-dEGCG unless specified.

Since EGCG has a polyphenol structure capable of interacting with SU via hydrophobic interaction and π-π stacking, it was anticipated that EGCG enriched in the core of micellar nanocomplexes would provide a favorable environment for SU entrapment. In addition, the surface-exposed PEG chains would form a highly hydrated shell around the micellar nanocomplexes to avoid clearance by the RES, thereby allowing prolonged circulation in the blood stream and reduction of side effects.

Characterization of SU/PEG-mEGCG Micellar Nanocomplexes

Figure 11:
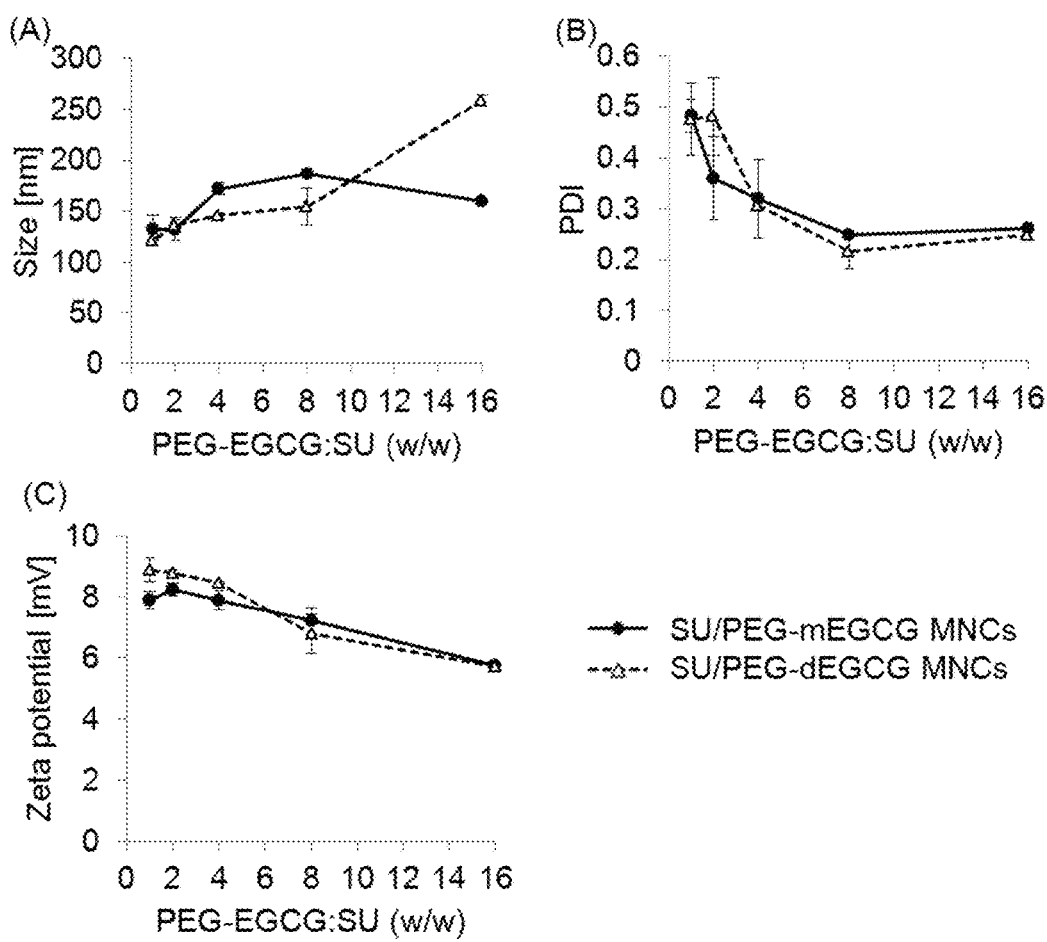
FIG. 11 refers to graphs showing (A) size, (B) PDI and (C) zeta potential of SU/PEG-EGCG micellar nanocomplexes at different PEG-EGCG:SU weight ratios.

The hydrodynamic diameters, size distribution and surface charge of SU/PEG-mEGCG micellar nanocomplexes were evaluated by dynamic light scattering (DLS) (Zetasizer Nano ZS, Malvern, UK). The measurements were conducted in triplicates in water at 25° C. FIG. 11A shows the hydrodynamic diameter of the micellar nanocomplexes prepared at different PEG-EGCG:SU weight ratios. Notably, the micellar nanocomplexes were produced in the size range of 130-250 nm. The nanometer size would be favorable in prolonging circulation and in tumor targeting via the EPR effect. The characteristics of micellar nanocomplexes were controlled by varying the PEG-EGCG:SU weight ratios. FIG. 11B shows that micellar nanocomplexes formed at PEG-EGCG:SU weight ratios of 8 and 16 were highly monodisperse. The micellar nanocomplexes decreased in their positive charge as the PEG-EGCG:SU weight ratio increased (FIG. 11C). Their slightly positive surface charge was attributed to the encapsulation of positively charged SU molecules.

To measure the drug loading efficiency and amount, 10 μL of micellar nanocomplexes in water was dissolved in 990 μL of DMF, and the absorbance of SU was measured at 431 nm using a Hitachi U-2810 ultraviolet-visible (UV-Vis) spectrophotometer (Japan). The calibration curve obtained with the SU standard solutions was used for determining the loading efficiency and amount.

Figure 12:
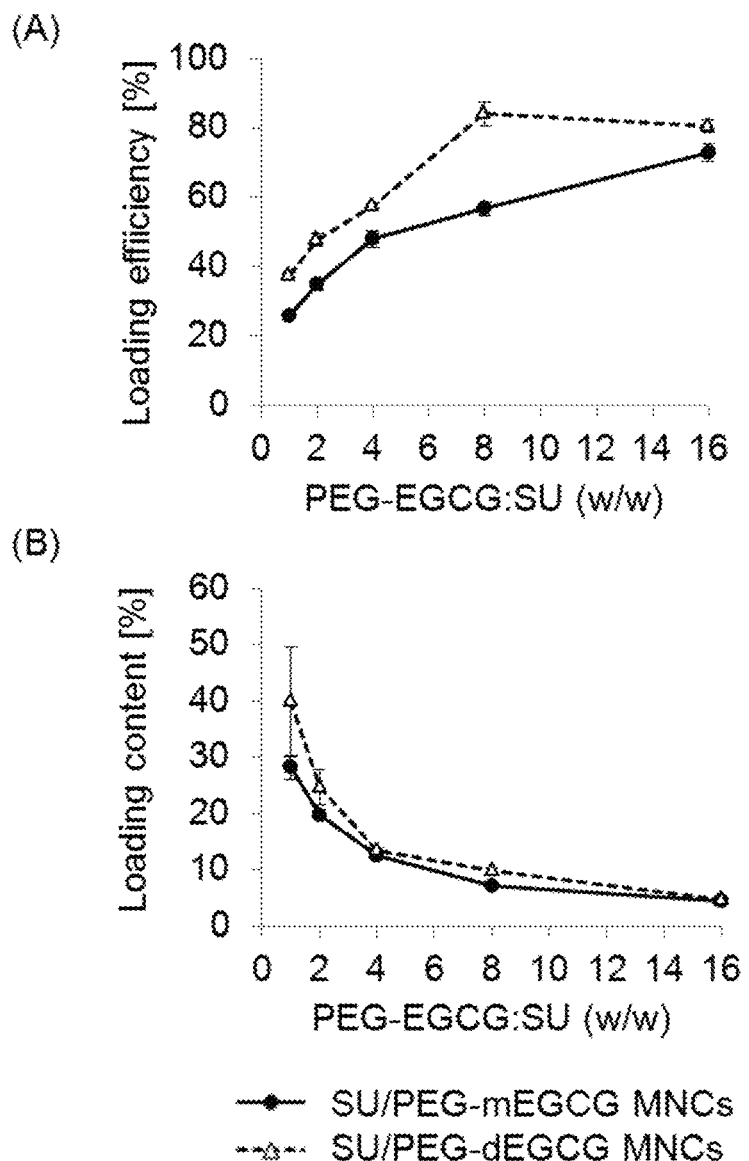
FIG. 12 refers to graphs showing (A) drug loading efficiency and (B) drug loading content of SU/PEG-EGCG micellar nanocomplexes prepared at different PEG-EGCG:SU weight ratios.

FIG. 12 shows the drug loading efficiency and drug loading content of SU/PEG-EGCG micellar nanocomplexes. As the PEG-EGCG:SU weight ratio increased from 1 to 16, the drug loading efficiency increased from ~30% to ~80%. The loading efficiency of SU/PEG-dEGCG micellar nanocomplexes was higher than SU/PEG-mEGCG micellar nanocomplexes, indicating greater interaction of SU with PEG-dEGCG as compared to with PEG-mEGCG. It was also found that the loading efficiency of micellar nanocomplexes was related to the amount of unloaded SU precipitate before filtration. When the PEG-EGCG:SU weight ratio was increased to 8, no SU precipitates were found. As expected, the loading content of the micellar nanocomplexes decreased as the PEG-EGCG:SU weight ratio increased due to the higher content of PEG-EGCG in the micellar nanocomplexes.

SU Release Study

The drug release profile of SU/PEG-EGCG micellar nanocomplexes was further investigated under physiological condition (phosphate-buffered saline (PBS), pH 7.3 at 37° C.). For SU release experiments, 0.5 mL of SU/PEG-EGCG micellar nanocomplexes (0.4 mg mL$^{-1}$) was placed in dialysis tubes (MWCO=2,000 Da). The tubes were immersed in 25 mL of PBS in a shaking incubator at 37° C.

At a given time point, 1 mL of the release medium was collected and then replaced with an equivalent volume of fresh PBS. The SU amount released into the medium was determined by measuring the absorbance at 431 nm using a Hitachi U-2810 spectrophotometer.

Figure 13:
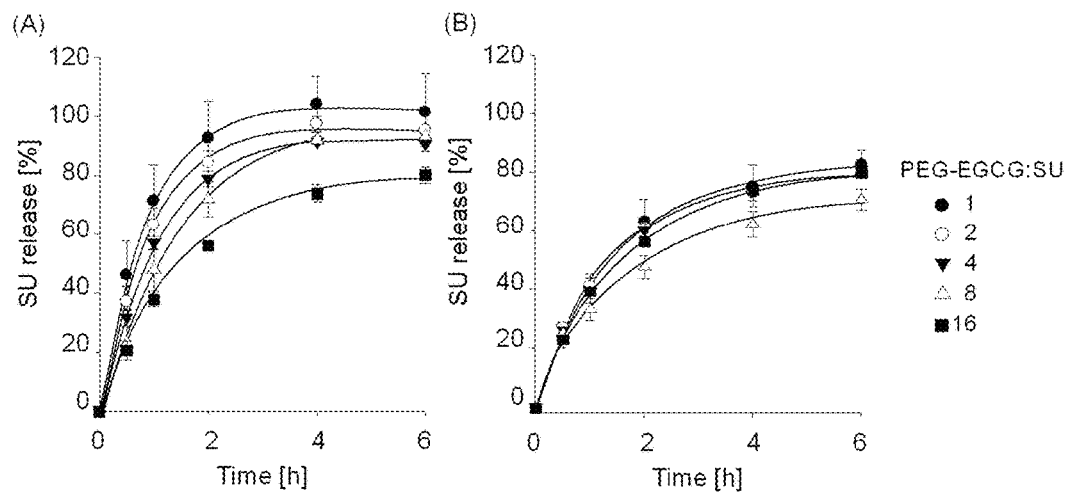
FIG. 13 refers to graphs showing the in vitro drug release profile of (A) SU/PEG-mEGCG micellar nanocomplexes and (B) SU/PEG-dEGCG micellar nanocomplexes at different PEG-EGCG:SU weight ratios in PBS (pH 7.3) at 37° C.

As shown in FIG. 13, the micellar nanocomplexes exhibited a sustained release of SU in PBS, which could be attributed to the strong interaction between EGCG and SU within the micellar nanocomplexes. In addition, hardly any burst release was observed, suggesting that SU molecules were stably encapsulated in the micellar nanocomplexes. SU/PEG-mEGCG micellar nanocomplexes showed faster and more SU release as compared to SU/PEG-dEGCG micellar nanocomplexes due to the weaker interaction between SU and mEGCG moieties. The release rate and amount also depended on the PEG-EGCG:SU weight ratio. For the SU/PEG-mEGCG micellar nanocomplexes, both release rate and amount decreased as the PEG-EGCG:SU weight ratio increased. The PEG-EGCG:SU weight ratio did not significantly affect the release rate and amount in the SU/PEG-dEGCG micellar nanocomplexes, except that a slower and lower release was associated with a PEG-EGCG:SU weight ratio of 8.

In Vivo Therapeutic Study

To study the toxicity and therapeutic effect, in vivo studies were conducted on the micellar nanocomplexes. A subcutaneous renal cell carcinoma model was established. Adult female Balb/c athymic, immunoincompetent nude mice (average weight=19 g, age=6-8 weeks) were used.

To study the therapeutic effect of SU/PEG-EGCG micellar nanocomplexes by intravenous injection, a xenograft tumor model was established by inoculating $6 \times 10^6$ A498-luc cells subcutaneously into the root of the left thigh of the mouse. On day 6 after tumor inoculation, the animals were divided into four groups for tail vein injection of various solutions (n=8 per group) twice weekly for 5 weeks, while one group received daily SU gavaging at 60 mg/kg. For the tail vein injection, a volume of 200 µl of sample solution was used.

To monitor bioluminescent signals from A498-luc cells, isoflurane gas-anesthetized animals were injected intraperitoneally with 200 µl of D-luciferin (5 mg ml$^{-1}$, Promega) in PBS, and placed on a warmed stage (30° C.) inside the camera box of the IVIS imaging system (Xenogen, Alameda, Calif., USA) with a CCD camera. Luminescent images were taken 20 minutes after luciferin injection as a 30-s acquisition. The light emitted from A498-luc cells was digitized and electronically displayed as a pseudocolor overlay onto a grayscale image of the animal. Images and measurements of luminescent signals were acquired and analyzed with the Xenogen imaging software v3.2 and quantified as photons/s. Tumor size and body weight were measured on a weekly basis. All handling and care of animals were performed according to the Guidelines on the Care and Use of Animals for Scientific Purposes issued by the National Advisory Committee for Laboratory Animal Research, Singapore.

All data were represented as mean±standard error of the mean (SEM). The statistical significance of differences between mean values was determined by Student's t-test. Multiple comparisons were evaluated by ANOVA with Bonferroni's multiple comparison tests using SigmaStat 3.5. A P-value of <0.05 was considered to be statistically significant.

SU/PEG-mECGC micellar nanocomplexes (with PEG-EGCG:SU weight ratios of 8 and 16) and SU/PEG-dEGCG micellar nanocomplexes (with PEG-EGCG:SU weight ratio of 8) were selected for the in vivo studies on the basis of micellar nanocomplex size, size distribution and surface charge. SU/PEG-mEGCG micellar nanocomplexes were intravenously injected twice weekly for 5 weeks, and one group received daily SU gavaging at 60 mg/kg. The oral drug dose of 60 mg/kg per day was selected based on prior reports that demonstrated the optimal preclinical dose of SU for antitumor efficacy in mice to be 40-80 mg/kg per day. For our studies, the 60 mg/kg per day dose represented an efficacious antitumor dose, as other studies indicated that a dose of <40 mg/kg per day to be subefficacious, and a dose of 120 mg/kg per day would test the effects of further elevated administration of the drug.

Figure 14:
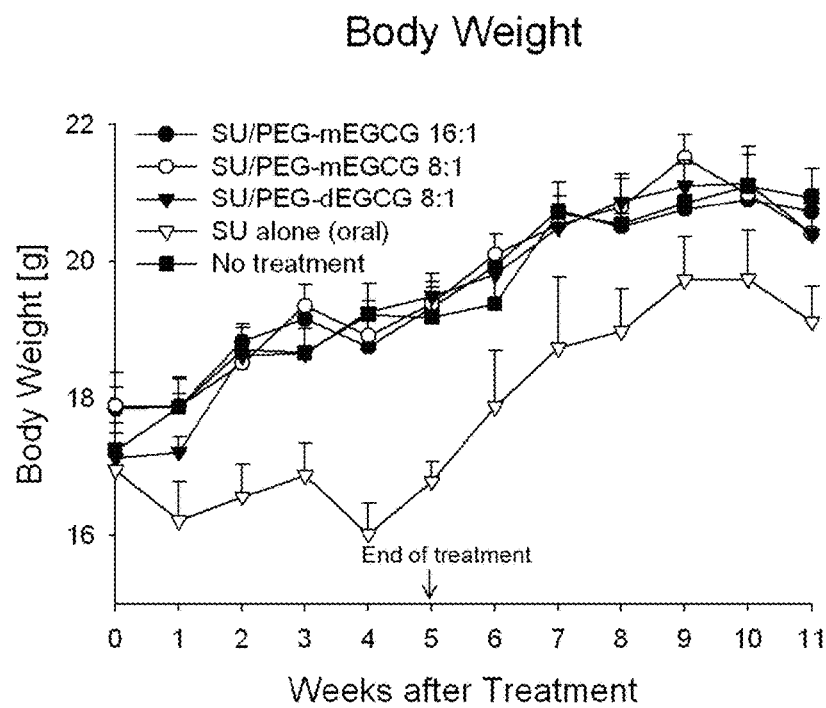
FIG. 14 is a graph showing weekly body weight measurements in mice receiving daily oral SU treatment (60 mg/kg) compared to those receiving SU/PEG-EGCG micellar nanocomplexes (with the specified PEG-EGCG:SU weight ratios) and the control group.
Figure 15A:
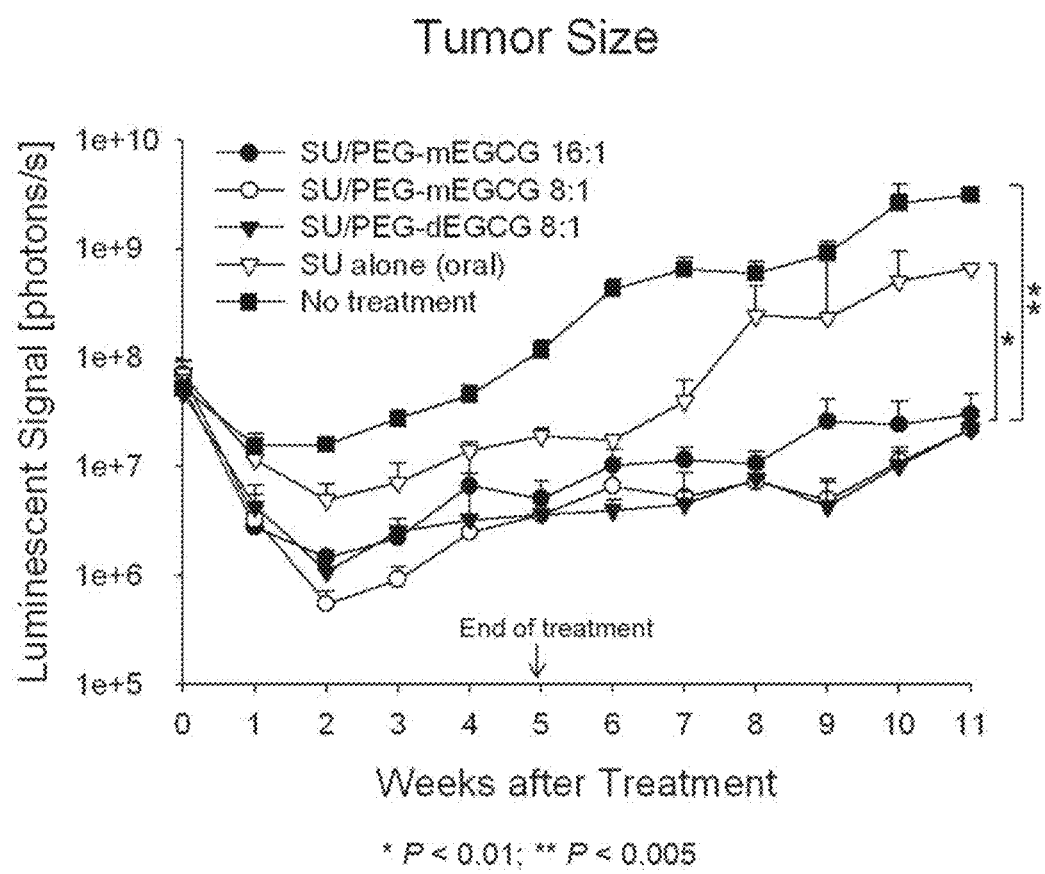
FIGS. 15(A)-15(B) refer to images that show (A) tumor size (as quantified by luminescent signal) and (B) luminescent image of mice with SU/PEG-EGCG micellar nanocomplex (with the specified PEG-EGCG:SU weight ratio) treatment, oral SU treatment, or no treatment.
Figure 15B:
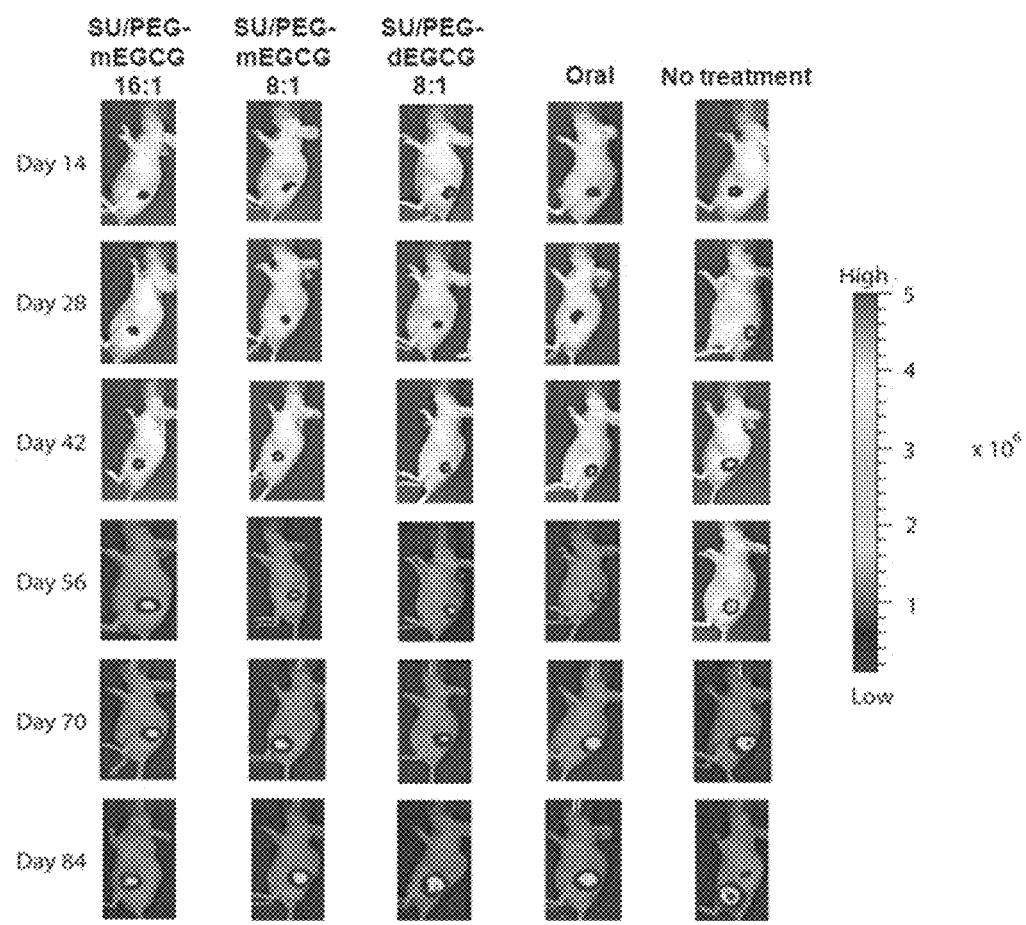

FIG. 14 shows significant weight loss in the group receiving oral free SU one week after commencement of treatment. This was not observed in the other groups receiving SU/PEG-EGCG micellar nanocomplex treatment. Antitumor effect was enhanced when SU/PEG-EGCG micellar nanocomplexes were administered twice weekly, as compared to daily SU oral therapy (FIG. 15). This antitumor effect with SU/PEG-EGCG micellar nanocomplexes was achieved at nearly one-tenth the concentration of the oral dose. The inhibitory effect of SU/PEG-EGCG micellar nanocomplex was maintained for a substantial period even when the therapy was halted after 5 weeks. The rate of tumor regrowth was much faster in the group receiving oral treatment, as compared to the groups receiving micellar nanocomplex treatment.

Figure 16:
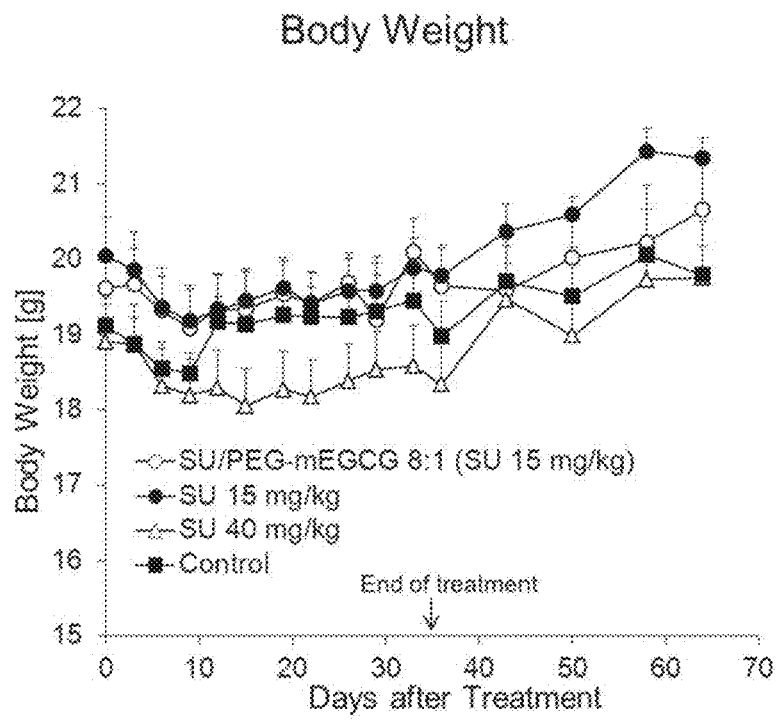
FIG. 16 is a graph showing body weight measurements in mice receiving daily oral SU treatment (40 and 15 mg/kg) compared to those receiving SU/PEG-mEGCG 8:1 micellar nanocomplex and the control group.
Figure 17:
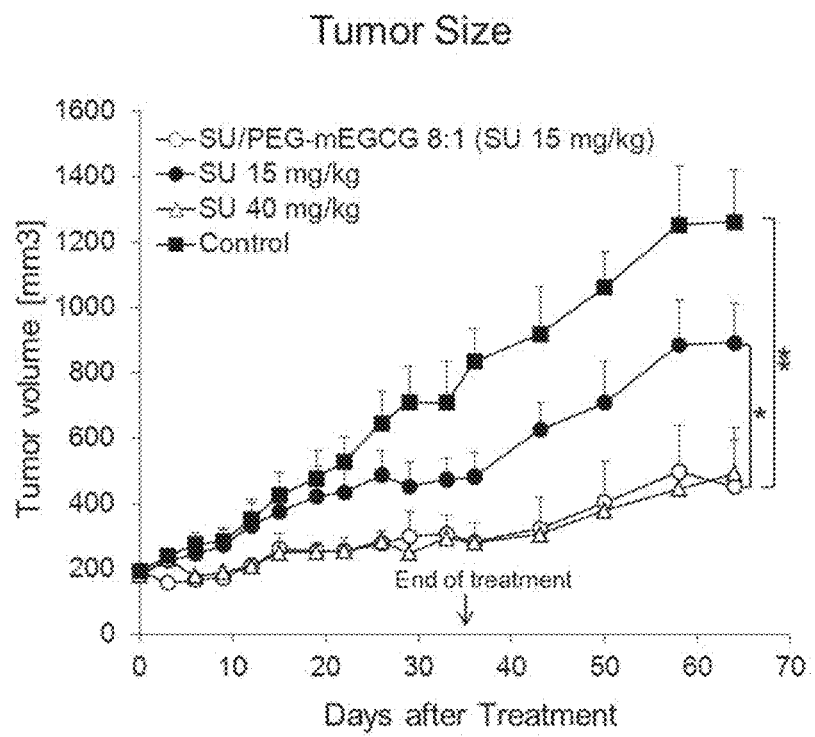
FIG. 17 is a graph showing tumor size of mice with oral SU/PEG-mEGCG 8:1 micellar nanocomplex treatment, oral SU treatment, or no treatment.

To investigate the therapeutic effect of SU/PEG-mEGCG MNC via oral administration, a xenograft tumor model was established by inoculating $4 \times 10^6$ ACHN cells suspended in 100 µl of PBS and 100 µl of Matrigel (BD Bioscience) subcutaneously into the root of the right thigh of the mouse. Once the tumors reached a volume of 200 mm$^3$, the animals were divided into four groups for oral gavage of various solutions (n=8 per group) daily for 5 weeks: control (citrate buffer pH5), SU/PEG-mEGCG 8:1 (SU at 15 mg/kg), SU at 15 and 40 mg/kg. Tumors were measured twice weekly with a digital caliper, and the tumor volumes (mm$^3$) were calculated from the following formula: volume=(length× width$^2$)/2 (FIGS. 16 and 17).

As it has been shown that the oral SU dose of 60 mg/kg per day is too toxic, the oral SU dose was reduced to 40 mg/kg per day in this disclosure. This oral dose of 40 mg/kg per day is the optimal preclinical dose for antitumor efficacy in mice (40-80 mg/kg per day) based on prior reports. FIG. 16 shows significant weight loss in the group receiving SU at 40 mg/kg during treatment. This was not observed in the other groups receiving SU/PEG-mEGCG MNC 8:1 and SU at 15 mg/kg treatment. With the same SU dose at 15 mg/kg, SU/PEG-mEGCG MNC showed a significantly higher therapeutic effect when compared to SU alone (FIG. 17). This antitumor effect with SU/PEG-mEGCG MNC was achieved at less than half the concentration of the optimal oral SU dose at 40 mg/kg. The inhibitory effect of SU/PEG-mEGCG MNC was maintained for a substantial period even when the therapy was halted after 5 weeks.

EPR effect considers the anatomical-physiological nature of tumor blood vessels that facilitate transport of macromolecules of >40 kDa that selectively leak out from tumor vessels and accumulate in tumor tissue. Most solid tumors have blood vessels with defective architecture, which usually results in extensive amounts of vascular permeability. This does not occur in normal tissues. The present invention discloses the use of SU/PEG-mEGCG micellar nanocomplexes via both intravenous and oral administrations as a possible therapy for ccRCC for the first time. It has been observed that EGCG interacted with SU, and pharmacokinetic studies in rat showed that administration of EGCG markedly reduced plasma concentrations of SU. The reported interaction of green tea with SU and the EPR effect of micellar nanoparticles in various tumors suggested the possibility of using PEG-EGCG as a nanoparticle carrier for SU delivery. In glioblastoma, a highly angiogenic tumor, anti-angiogenic therapy has shown a high but transient efficacy. Such tumor stimulates the formation of new blood vessels through processes driven primarily by VEGF, but the resulting vessels are structurally and functionally abnormal. The use of SU/PEG-EGCG micellar nanocomplexes might potentially enhance the anti-angiogenic activity in such cases.

INDUSTRIAL APPLICABILITY

The micellar nanocomplexes may be applied for use in systemic administration of doxorubicin for cancer treatment.

The micellar nanocomplexes may be used as a nanoparticle carrier for SU delivery. In glioblastoma, a highly angiogenic tumor, anti-angiogenic therapy has shown a high but transient efficacy. Such tumor stimulates the formation of new blood vessels through processes driven primarily by VEGF, but the resulting vessels are structurally and functionally abnormal. The use of micellar nanocomplexes comprising SU may potentially enhance the anti-angiogenic activity in such cases.

The micellar nanocomplexes may be used for sustained release of therapeutic agents when administered systemically, or as a delivery system for therapeutic agents in targeted sites.

The miscellar nanocomplexes may be used for encapsulation of various therapeutic agents for different kinds of cancer treatment.

The miscellar nanocomplexes may also be used for encapsulation of various therapeutic agents for non-cancerous treatment. This may include small molecules for antibiotics and other medical applications.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A polymer-flavonoid conjugate comprising a polymer bonded to the B ring of a flavonoid.

2. The polymer-flavonoid conjugate of claim 1, wherein said polymer is selected from the group consisting of a polysaccharide, polyacrylamide, poly(N-isopropylacrylamide), poly(oxazoline), polyethylenimine, poly(acrylic acid), polymethacrylate, poly(ethylene glycol), poly(ethylene oxide), poly(vinyl alcohol), poly(vinylpyrrolidinone), polyethers, poly(allylamine), polyanhydrides, poly(β-amino ester), poly(butylene succinate), polycaprolactone, polycarbonate, polydioxanone, poly(glycerol), polyglycolic acid, poly(3-hydroxypropionic acid), poly(2-hydroxyethyl methacrylate), poly(N-(2-hydroxypropyl)methacrylamide), poly-lactic acid, poly(lactic-co-glycolic acid), poly(ortho esters), poly(2-oxazoline), poly(sebacic acid), poly(terephthalate-co-phosphate) and copolymers thereof.

3. The polymer-flavonoid conjugate of claim 1, wherein said flavonoid is selected from the group consisting of (−)-epicatechin, (+)-epicatechin, (−)-catechin, (+)-catechin, epicatechin gallate, epigallocatechin, epigallocatechin gallate, Fisetinidol, Gallocatechin, Gallocatechin gallate, Mesquitol and Robinetinidol, ellagitannin, gallotannin, oolongtheanin, phlorotannin, tannin, theacitrin, theadibenzotropolone, theaflavin, theanaphthoquinone, thearubigins, theasinensin and mixtures thereof.

4. The polymer-flavonoid conjugate of claim 1, wherein said polymer is conjugated to a flavonoid via a linker selected from the group consisting of a thioether, imine, amine, azo and 1,2,3-triazole group.

5. The polymer-flavonoid conjugate of claim 1, where said polymer is poly(ethylene glycol), said flavonoid is epigallocatechin-3-gallate and said linker is thioether.

6. The polymer-flavonoid conjugate of claim 5, wherein said conjugate has the following formula

[Chem. 2]

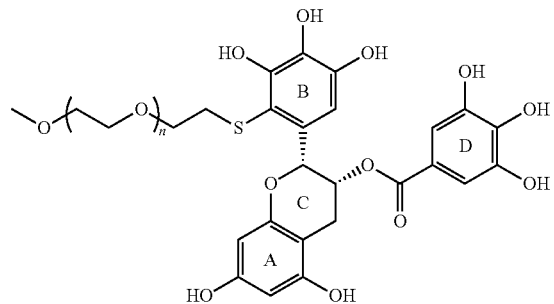

wherein n is in the range of 20 to 910.

7. The method for forming the polymer-flavonoid conjugate of claim 1 comprising the step of conjugating said flavonoid with said polymer via nucleophilic addition under basic conditions, wherein said polymer has a free nucleophilic group.

8. The method of claim 7, wherein said conjugating step is undertaken at a reaction time of between 1 to 24 hours.

9. The method of claim 7, further comprising the step of conducting the conjugating step in a solvent that substantially prevents aggregation of said flavonoid.

10. The method of claim 7, further comprising the step of adding a scavenging agent to prevent H2O2-mediated oxidation of said nucleophilic group to thereby increase the efficiency of said conjugating step.

11. The method of claim 7, wherein said basic conditions is in the pH range of more than 7 to 10.

12. The method of claim 7, wherein said nucleophilic group is selected from the group consisting of a thiol, an amine, a diazoalkane and an azide.

* * * * *